(12) United States Patent
Kitabwalla et al.

(10) Patent No.: US 7,361,360 B2
(45) Date of Patent: Apr. 22, 2008

(54) METHOD OF TREATING CANCER CELLS TO CREATE A MODIFIED CANCER CELL THAT PROVOKES AN IMMUNOGENIC RESPONSE

(75) Inventors: Moiz Kitabwalla, Livermore, CA (US); Hassibullah Akeefe, San Ramon, CA (US)

(73) Assignee: Lipid Sciences, Inc., Pleasanton, CA (US)

( * ) Notice: Subject to any disclaimer, the term of this patent is extended or adjusted under 35 U.S.C. 154(b) by 0 days.

(21) Appl. No.: 11/493,936

(22) Filed: Jul. 26, 2006

(65) Prior Publication Data

US 2007/0026006 A1     Feb. 1, 2007

Related U.S. Application Data

(60) Provisional application No. 60/702,691, filed on Jul. 27, 2005.

(51) Int. Cl.
*A61K 39/00* (2006.01)
*A01N 1/00* (2006.01)

(52) U.S. Cl. ..................... 424/277.1; 435/1.1
(58) Field of Classification Search ..................... None
See application file for complete search history.

(56) References Cited

U.S. PATENT DOCUMENTS

2004/0202676 A1    10/2004   Rybudo et al.
2005/0004004 A1*    1/2005   Bellotti et al. ................. 514/2

OTHER PUBLICATIONS

Bachmann, M.F., Wolint, P., Schwarz, K., and Oxenius, A. Recall proliferation potential of memory CD8+ T cells and antiviral protection. 2005. Journal of Immunology, vol. 175, pp. 4677-4685.*

Efferson, C.L., Kawano, K., Tsuda, N., Palese, P., Garcia-Sastre, A., and Ioannides, C.G. Stimulation of human T cells by an influenza A vector expressing a CTL epitope from the HER-2/neu protooncogene results in higher numbers of antigen-specific TCRhi cells than stimulation with peptide. 2005. Anticancer Research, vol. 25, pp. 715-724.*

Wheeler, C.M. Preventative vaccines for cervical cancer. 1997. Salud Publica de Mexico, vol. 39, No. 4.*

Stedman's Medical Dictionary. On-line version, 2000. Vaccine definition.*

Fields, et al., "Murine Dendritic Cells Pulsed With Whole Cell Tumor Lysates Mediate Potent Antitumor Immune Responses *in Vitro* and *in Vivo*," Natl. Acad. Sci USA, vol. 95, pp. 9482-9487 (1998).

Kitabwalla, et al., "Enhancement of Cell Mediated Immune Responses Using Lipid Depleted Lentivirus as Immunogen: A Novel Approach for Inducing Recognition of New Viral Epitopes," Vaccine, vol. 23, pp. 4666-4677 (2005).

* cited by examiner

*Primary Examiner*—Larry R. Helms
*Assistant Examiner*—Anne M. Gussow
(74) *Attorney, Agent, or Firm*—Kilpatrick Stockton LLP

(57) ABSTRACT

The present invention relates to a delipidation method employing a solvent system useful for extracting lipids from cancer cells, thereby creating a modified cancer cell particle. Upon delipidation of the cancer cells, a portion of the cancer cell antigens remain intact. These exposed antigens, or epitopes, foster and promote antibody production. The resulting modified cancer cell particle, or portions of the cancer cell, initiate a positive immunogenic response when administered to an animal or human and help to treat, prevent or delay the onset of cancer. The present invention provides autologous and heterologous vaccine compositions comprising the modified cancer cell with a pharmaceutically acceptable carrier. The present invention provides method of administering these vaccines to treat, prevent or delay the onset of cancer.

18 Claims, 7 Drawing Sheets

Immature DC Uptake of B16-F10 Cells (PE labelled)

A = Dendritic Cells

B = Dendritic Cells + Delipidated B16-F10 (cancer cells)

C = Delipidated B16-F10 (cancer cells)

Immature DC Uptake of B16-F10 Cells (PE labelled)

A = Dendritic Cells

B = Dendritic Cells + Delipidated B16-F10 (cancer cells)

C = Delipidated B16-F10 (cancer cells)

METHOD OF TREATING CANCER CELLS TO CREATE A MODIFIED CANCER CELL THAT PROVOKES AN IMMUNOGENIC RESPONSE

PRIOR RELATED APPLICATIONS

The present application claims the benefit of priority to U.S. provisional patent application Ser. No. 60/702,691 filed Jul. 27, 2005.

FIELD OF THE INVENTION

The present invention provides a delipidation method employing a solvent system useful for extracting lipids from cancer cells, thereby creating a modified cancer cell particle. Upon delipidation of the cancer cells, some of the cancer cell antigens remain intact. These exposed antigens, or epitopes, foster and promote antibody production. The resulting modified cancer cell with reduced lipid content, or portions of the cancer cell, initiate a positive immunogenic response when administered to an animal or human and help to treat, prevent or delay the onset or progression of cancer. The present invention provides autologous and heterologous vaccine compositions comprising the modified cancer cell with a pharmaceutically acceptable carrier. The present invention provides a method of administering these vaccines to treat, prevent or delay the onset or progression of cancer.

BACKGROUND OF THE INVENTION

Introduction

Cancers, of varied etiology, affect billions of animals and humans each year and inflict an enormous economic burden on society. Cancers can be defined as an abnormal lump, mass of tissue, or cancerous cells generated from excessive cell division, which is either benign or malignant. Cancers include all those cancers known to physicians of ordinary skill in the medical arts, particularly physicians of skill in oncology. Cancers include, but are not limited to, those arising from ectodermal, mesodermal and endodermal cells and include cancers of the immune system, the endocrine system, the central nervous system, the respiratory system, the reproductive system, the gastrointestinal system, and the integument. Such cancers include those generated by AIDS-related cancers, adrenocortical cancer, anal cancer, bladder cancer, bowel cancer, brain and central nervous system cancers, breast cancer, carcinoid cancers, cervical cancer, chondrosarcoma, choriocarcinoma, colorectal cancer, endocrine cancers, endometrial cancer, Ewing's sarcoma, eye cancer, gastric cancer, gastrointestinal cancer, genitourinary cancers, glioma, gynecological cancer, head and neck cancer, hepatocellular cancer, Hodgkin's disease, hypopharyngeal cancer, islet cell cancer, Kaposi's sarcoma, kidney cancer, laryngeal cancer, leukemia, liver cancer, lung cancer, lymphoma, melanoma, basal cell carcinoma, mesothelioma, myeloma, nasopharyngeal cancer, neuroblastoma, non-Hodgkin's lymphoma, esophagael cancer, osteosarcoma, ovarian cancer, pancreatic cancer, pituitary cancer, renal cell carcinoma, prostate cancer, retinoblastoma, rhabdomyosarcoma, sarcoma, skin cancer, squamous cell carcinoma, stomach cancer, testicular cancer, thymus cancer, thyroid cancer, transitional cell cancer, trophoblastic cancer, uterine cancer, vaginal cancer, Waldenstrom's macroglobulinemia, Wilm's cancer, among other tumors and forms of cancer.

As with normal cells, cancer cells contain lipid as a major component of the plasma membrane that surrounds them. While it is not fully known why cancer cells form, in general, cancers appear to be caused by the abnormal regulation of cell division. This could be caused by abnormalities of the immune system, genetic abnormalities, radiation-caused mutations, certain viruses, sunlight, and cancer-causing agents such as tobacco, benzene, and other chemicals. When a patient is inflicted with a cancer, he incurs a number of symptoms, including fevers, chills, night sweats, weight loss, loss of appetite, fatigue, malaise, shortness of breath, chest pain, diarrhea, blood in the stool or urine, among other ailments.

Eliminating cancer from a patient's body is challenging because, although cancerous cells proliferate in an uncontrolled manner, the cells do not necessarily appear to be "foreign" to the body and, therefore, are difficult to target. Existing cancer treatments tend to be non-sufficiently targeted to the cancer cells and, therefore, are very destructive to a patient's healthy tissue. Such treatments include X-rays, chemotherapy, proton therapy, surgery or combinations thereof. It would be preferred if the body's immune system could be incited to exhibit a positive immune response against these cancer cells.

The human immune system is composed of various cell types that collectively protect the body from different foreign agents. The immune system provides multiple means for targeting and eliminating foreign elements, including humoral and cellular immune responses, participating primarily in antigen recognition and elimination. An immune response to foreign elements requires the presence of B-lymphocytes (B cells) or T-lymphocytes (T cells) in combination with antigen-presenting cells (APC), which are usually macrophages or dendrite cells. The APCs are specialized immune cells that capture antigens. Once inside an APC, antigens are broken down into smaller fragments called epitopes—the unique markers carried by the antigen surface. These epitopes are subsequently displayed on the surface of the APCs and are responsible for triggering an antibody response in defense of foreign agents.

In a humoral immune response, when an APC displaying antigens (in the form of unique epitope markers) foreign to the body are recognized, B cells are activated, proliferate and produce antibodies. These antibodies specifically bind to the antigens present on the APC. After the antibody attaches, the APC engulfs the entire antigen and kills it. This type of antibody immune response is primarily involved in the prevention of various infections.

In a cellular immune response, on recognizing the APC displaying a foreign antigen, the T cells are activated. There are two steps in the cellular immune response. The first step involves activation of cytotoxic T cells (CTL) or CD8+ T killer cells that proliferate and kill target cells that specifically represent the antigens presented by APC. The second involves helper T cells (HTL) or CD4+ T cells that regulate the production of antibodies and the activity of CD8+ cells. The CD4+ T cells provide growth factors to CD8+ T cells that allow them to proliferate and function efficiently.

While cancer cells are now known to express cancer-associated antigens, they are often able to evade an immune response because of their ability to hide cancer antigens from the immune system and/or because the exposed antigens are normal, nonmutated differentiation molecules or proteins which the human immune system normally recognizes or tolerates. To effectively use immunotherapy to treat a cancer, a patient must have, or be provided with, a sufficient number of cancer-reactive lymphocytes, which can both reach the cancer site and have effector mechanisms to destroy the cancer cells.

To date, immune responses generated by cancer vaccines have been unable to overcome the escape mechanisms of cancers, including the ability to target and infiltrate cancers, to deal with the loss of antigenic expression by the cancer, to handle the inability of the cancer to activate anti-cancer precursors, and to address the local presence of immunosuppressive factors. Some success has been observed in cell-transfer therapies where autologous lymphocytes are sensitized to cancer cells ex vivo and then infused back into the patient.

One adjuvant for cancer vaccine immunotherapy uses dendritic cells (DC) that are highly potent antigen-presenting cells to provoke a positive anti-cancer immune response in patients. Dendritic cells express MHC class I and MHC class II molecules, co-stimulatory molecules and adhesion molecules that provide signals for the stimulation of naive T cells, CD4+ T-helper cells, CD8+ cytotoxic T lymphocytes (CTLs), natural killer (NK) and thymic derived NK cells (NKT) cells. DC have the capacity to take up various types of molecules. Consequently, DC can be loaded with tumor-associated antigens (TAAs) in various forms and administered as vaccines.

One DC-based approach uses DC-cancer cell hybrids generated by fusion of cancer cells with DC to combine sustained cancer antigen expression with the antigen-presenting and immune stimulatory capabilities of DC. In animal models, immunization with DC-cancer cell hybrids can provide some form of anti-cancer protection or eradicate established disease. Hybrids of autologous DC comprised of cancer cell lines or primary human cancer cells (including breast carcinoma cells) have been shown to induce CTL responses against autologous cancer cell types in vitro. Recent phase I clinical trials for the treatment of renal cell carcinoma and glioma have demonstrated that vaccination with DC-cancer cell hybrids can safely induce anti-cancer immune responses in patients. Traditional fusion technology using polyethylene glycol (PEG) is hampered by a lack of reproducibility and difficulties in method standardization. As an alternative, electrofusion has been used for production of DC-cancer cell hybrids." See Akporiaye, et al., "Pre-Clinical Studies of Dendritic Cell-Tumor Cell Fusion Vaccines to Treat Breast Cancer".

Accordingly, what is needed is an effective delipidation process via which a cancer cell is modified, rather than destroyed, and invokes an autologous or heterologous immune response to prevent further proliferation of cancers.

What is needed is a therapeutic method and system for providing patients with modified cancer cells capable of initiating a protective immune response.

What is further needed is a way of identifying and revealing tumor-associated antigens that can be used with existing DC-cancer cell therapy techniques to provoke a positive immune response in a patient.

What is needed is a method for promoting antibody production comprising administering to a patient a modified cancer cell capable of initiating a protective immune response.

SUMMARY OF THE INVENTION

The present invention solves the problems described above by providing a simple, effective and efficient method for treating cancer, preventing cancer, delaying the onset of cancer or delaying the progression of cancer via administration of the vaccine described herein. The method of the present invention is effective in modifying the lipid structure of a cancer cell utilizing an solvent system which does not have deleterious effects on the structure of cancer-associated antigens. The present invention employs an optimal solvent/energy system to create, via delipidation, a modified cancer cell that has its lipid envelope at least partially removed, thereby exposing or modifying cancer-associated antigens that, either alone or in the form of a DC-cancer cell hybrid, can generate a positive immunologic response in a patient, providing that patient with some degree of protection against the proliferating cancer, preventing the occurrence or reoccurrence of the cancer, or delaying the onset of cancer.

The present invention is also effective in producing an autologous, patient-specific vaccine against the cancer, by treating a biological fluid containing the cancer cell such that the cancer cell is present in a modified form. To create the vaccine, a cancer sample is removed from the patient (i.e. a biopsy is performed or a blood or other sample is removed containing the cancer cells), cancer cells are isolated and partially delipidated using an optimal solvent system which retains the structural integrity of cancer cell antigens. In one embodiment, a cancer cell, treated in this manner in order to create a modified cancer cell with reduced lipid content, is administered to a recipient, such as an animal or a human, together with a pharmaceutically acceptable carrier, and optionally an adjuvant, in order to initiate an immune response in the animal or human and create antibodies that bind to the exposed epitopes of the delipidated cancer cell. In another embodiment, a cancer cell, treated in this manner in order to create a modified cancer cell, is for example, used to create a DC-cancer cell hybrid that is then administered to a recipient, such as an animal or a human, together with a pharmaceutically acceptable carrier, and optionally an adjuvant, in order to initiate an immune response in the animal or human and create antibodies that bind to the exposed epitopes of the delipidated cancer cell.

Thus an effective method is provided, by which new vaccines can be developed from lipid-containing cancer cells by partially removing the lipid envelope and exposing or modifying protein antigens hidden beneath the envelope, in turn generating a positive immune response when re-introduced, through various means, into the patient.

Cancers that may be treated with the present invention include all those cancers known to physicians of ordinary skill in the medical arts, particularly physicians of skill in oncology. Cancers include, but are not limited to, those arising from ectodermal, mesodermal and endodermal cells and include cancers of the immune system, the endocrine system, the central nervous system, the respiratory system, the reproductive system, the gastrointestinal system, and the integument. Such cancers include those generated by AIDS-related cancers, adrenocortical cancer, basal cell carcinoma, anal cancer, bladder cancer, bowel cancer, brain and central nervous system cancers, breast cancer, carcinoid cancers, cervical cancer, chondrosarcoma, choriocarcinoma, colorectal cancer, endocrine cancers, endometrial cancer, Ewing's sarcoma, eye cancer, gastric cancer, gastrointestinal cancer, genitourinary cancers, glioma, gynecological cancer, head and neck cancer, hepatocellular cancer, Hodgkin's disease, hypopharynx cancer, islet cell cancer, Kaposi's sarcoma, kidney cancer, laryngeal cancer, leukemia, liver cancer, lung cancer, lymphoma, melanoma, mesothelioma, myeloma, nasopharyngeal cancer, neuroblastoma, non-Hodgkin's lymphoma, esophagael cancer, osteosarcoma, ovarian cancer, pancreatic cancer, pituitary cancer, renal cell carcinoma, prostate cancer, retinoblastoma, rhabdomyosarcoma, sarcoma, skin cancer, squamous cell carcinoma, stomach cancer, testicular cancer, thymus cancer, thyroid cancer, transitional cell cancer, trophoblastic cancer, uterine cancer, vaginal cancer, Waldenstrom's macroglobulinemia, Wilm's cancer, among other tumors and forms of cancer.

Accordingly, it is an object of the present invention to provide a vaccine composition comprising a cancer cell with reduced lipid content and containing at least one cancer cell antigen in a pharmaceutically acceptable carrier and optionally an immunostimulant.

It is another object of the present invention to provide a vaccine composition comprising a cancer cell with reduced lipid content and containing at least one cancer cell antigen, and a dendritic cell, in a pharmaceutically acceptable carrier, and optionally an immunostimulant.

Accordingly, it is an object of the present invention to provide a method for treating a cancer cells in order to modify cancer cells contained therein to reduce their lipid content.

It is a further object of the present invention to provide a method for treating a cancer by administering cancer cells with reduced lipid content and containing at least one cancer cell antigen to an animal or a human.

Another object of the present invention is to provide a method for preventing cancer or delaying the onset of cancer by administering cancer cells with reduced lipid content and containing at least one cancer cell antigen to an animal or a human.

It is a further object of the present invention to provide a method for treating a cancer using a DC-cancer cell hybrid exhibiting cancer cell antigens, wherein the cancer cell has a reduced lipid content and contains at least one cancer cell antigen.

It is a further object of the present invention to provide a method for preventing cancer or delaying the onset of cancer using a DC-cancer cell hybrid exhibiting cancer cell antigens.

It is another object of the present invention to provide a method for exposing antigenic determinants on a cancer cell.

It is a further object of the present invention to completely or partially delipidate the cancer cell, thereby creating a modified cancer cell with reduced lipid content and containing at least one cancer cell antigen.

It is a further object of the present invention to partially, substantially or completely delipidate the cancer cell, while retaining the structural proteins or antigens of the cancer cell.

Yet another object of the present invention is to treat humans and animals with cancer using the method of the present invention using a vaccine comprising a DC-cancer cell hybrid wherein the cancer cell is a partially delipidated, modified cancer cell. The treatment may be administered to an animal or a human together with a pharmaceutically acceptable carrier and optionally an immunostimulant compound.

Still another object of the present invention is to treat humans and animals with cancer using the method of the present invention using a vaccine comprising a cancer cell with reduced lipid content and containing at least one cancer cell antigen. The treatment may be administered to an animal or a human together with a pharmaceutically acceptable carrier and optionally an immunostimulant compound.

Yet another object of the present invention is to treat humans and animals at risk of developing cancer with the method of the present invention by administering a vaccine comprising a DC-cancer cell hybrid wherein the cancer cell has reduced lipid content and contains at least one cancer cell antigen. The treatment may be administered to an animal or a human together with a pharmaceutically acceptable carrier and optionally an immunostimulant compound.

Still another object of the present invention is to treat humans and animals at risk of developing cancer with the method of the present invention by administering a cancer cell with reduced lipid and containing at least one cancer cell antigen.

Yet another object of the present invention is to treat humans and animals with cancer using the method of the present invention by administering a vaccine comprising cancer cell-associated antigens from a cancer cell with reduced lipid content which may be administered to an animal or a human together with a pharmaceutically acceptable carrier and optionally an immunostimulant compound, to initiate an immunogenic response in the animal or human.

Still another object of the present invention is to treat humans and animals at risk of developing cancer using the method of the present invention by administering a vaccine comprising a cancer cell with reduced lipid content and containing at least one cancer cell antigen which may be administered to an animal or a human together with a pharmaceutically acceptable carrier and optionally an immunostimulant compound, to initiate an immunogenic response in the animal or human.

Yet another object of the present invention is to provide a method for promoting antibody production comprising administering to the animal or human a cancer cell with reduced lipid content and containing at least one cancer cell antigen together with a pharmaceutically acceptable carrier in order to initiate an immunogenic response, resulting in the production of antibodies in the animal or human.

The present invention also provides a cancer cell with reduced lipid content and containing at least one cancer cell antigen, wherein this cancer cell initiates an immune response when administered to a patient and incites protection against a cancer.

The present invention also provides for a patient-specific modified cancer cells comprising a partially delipidated cancer cell, wherein the partially delipidated cancer cell is produced by exposing a non-delipidated cancer cell to a delipidation process and wherein the cancer cell with reduced lipid content comprises at least one exposed or modified patient-specific antigen that was not exposed or modified in the non-delipidated cancer cell.

The present invention also provides a method for making a vaccine comprising: contacting a lipid-containing cancer cell in a fluid with a first organic solvent capable of extracting lipid from the lipid-containing cancer cell; mixing the fluid and the first organic solvent for a time sufficient to extract lipid from the lipid-containing cancer cell; permitting organic and aqueous phases to separate; and collecting the aqueous phase containing a modified cancer cell with reduced lipid content wherein the modified cancer cell is capable of provoking a positive immune response when administered to a patient.

The present invention also provides a method for provoking a positive immune response in a patient having a plurality of lipid-containing cancer cells, comprising the steps of: obtaining a fluid containing the lipid-containing cancer cells from the patient; contacting the fluid containing the lipid-containing cancer cells with a first organic solvent capable of extracting lipid from the lipid-containing cancer cells; mixing the fluid and the first organic solvent: permitting organic and aqueous phases to separate; collecting the aqueous phase containing modified cancer cell particles with reduced lipid content; and introducing the aqueous phase containing the modified cancer cells with reduced lipid content into the animal or the human wherein the modified cancer cell with reduced lipid content provoke a positive immune response in the animal or the human.

Various modifications to the stated embodiments will be readily apparent to those of ordinary skill in the art, and the disclosure set forth herein may be applicable to other embodiments and applications without departing from the spirit and scope of the present invention.

BRIEF DESCRIPTION OF THE DRAWINGS

The accompanying drawings, which are incorporated in and form a part of the specification, illustrate preferred embodiments of the present invention.

DETAILED DESCRIPTION OF THE INVENTION

Definitions

Figure 1:
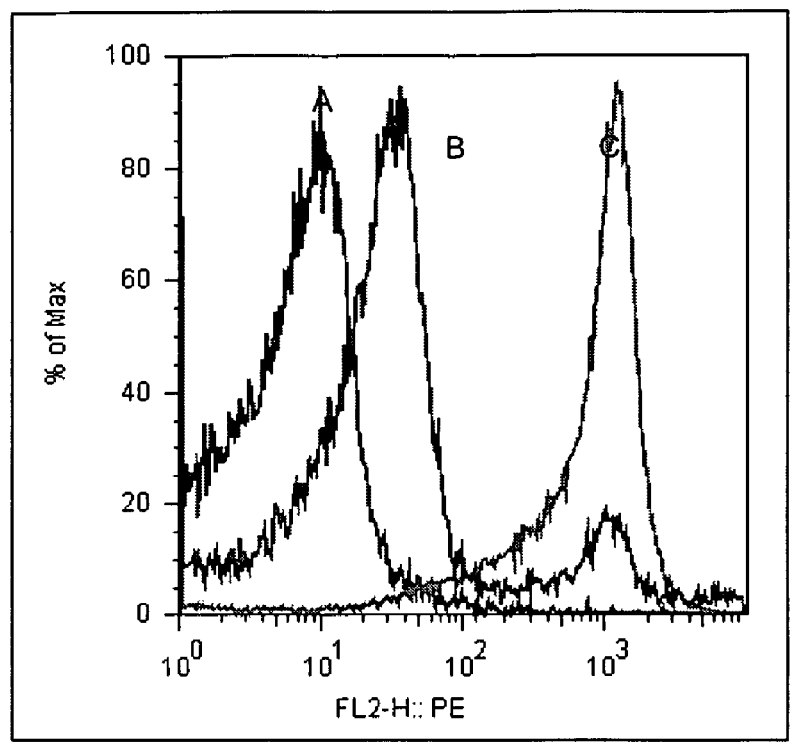
FIG. 1 depicts uptake of delipidated B16-F10 cancer cells by immature dendritic cells as determined by fluorescent activated cell sorting (FACS) (phycoerythrin (PE) labeled).

By the term "fluid" is meant any fluid containing cancer cells, including but not limited to, a biological fluid obtained from an organism such as an animal or human. Fluids which may be treated with the method of the present invention include but are not limited to the following: plasma; serum; lymphatic fluid; cerebrospinal fluid; peritoneal fluid; pleural fluid; pericardial fluid; various fluids of the reproductive system including but not limited to semen, ejaculatory fluids, follicular fluid and amniotic fluid; cell culture reagents such as normal sera, fetal calf serum or serum derived from any other animal or human; and immunological reagents such as various preparations of antibodies and cytokines. Such biological fluids obtained from an organism include but are not limited to other fluids contained within the organism. Other fluids may include laboratory samples containing cancer cells suspended in any chosen fluid. Other fluids include cell culture reagents, many of which include biological compounds such as fluids obtained from living organisms, including but not limited to "normal serum" obtained from various animals and used as growth medium in cell and tissue culture applications.

By the term "first extraction solvent" is meant a solvent, comprising one or more solvents, used to facilitate extraction of lipid from a lipid-containing cell or a fluid. The term "first extraction solvent" is used interchangeably with "first organic solvent" in the present application. This solvent will enter the fluid and remain in the fluid until being removed. Suitable first extraction solvents include solvents that extract or dissolve lipid, including but not limited to alcohols, hydrocarbons, amines, ethers, and combinations thereof. First extraction solvents may be combinations of alcohols and ethers. First extraction solvents include, but are not limited to n-butanol, di-isopropyl ether (DIPE), diethyl ether, and combinations thereof. In another embodiment, the first extraction solvent may optionally include a detergent.

The term "second extraction solvent" is defined as one or more solvents that may be employed to facilitate the removal of a portion of the first extraction solvent. Suitable second extraction solvents include any solvent that facilitates removal of the first extraction solvent from the fluid. Second extraction solvents include any solvent that facilitates removal of the first extraction solvent including but not limited to ethers, alcohols, hydrocarbons, amines, and combinations thereof. Preferred second extraction solvents include diethyl ether and di-isopropyl ether, which facilitate the removal of alcohols, such as n-butanol, from the fluid. The term "de-emulsifying agent" is a second extraction solvent that assists in the removal of the first extraction solvent which may be present in an emulsion in an aqueous layer. By the term "de-emulsifying agent" is meant an agent that assists in the removal of the first extraction solvent which may be present in an emulsion in an aqueous layer.

Detergents and surfactants known to one of ordinary skill in the art may be employed in combination with the at least first extraction solvent in the present invention. Such detergents and surfactants include, but are not limited to, various ionic and non-ionic detergents. Such detergents and surfactants include but are not limited to various forms of Triton or Tween.

The terms "modified cancer cell" and "cancer cell particle" are used interchangeably and describe a modified cancer cell, cancer cell particle or fragments thereof that results from application of the process of the present invention to cancer cells in order to reduce their lipid content.

The term "delipidation" refers to the process of removing at least a portion of a total concentration of lipids from a cancer cell.

The term "lipid" is defined as any one or more of a group of fats or fat-like substances occurring in humans or animals. The fats or fat-like substances are characterized by their insolubility in water and solubility in organic solvents. The term "lipid" is known to those of ordinary skill in the art and includes, but is not limited to, polar lipids, non-polar lipids, complex lipid, simple lipid, triglycerides, fatty acids, glycerophospholipids (phospholipids), sphingolipids, true fats such as esters of fatty acids, glycerol, cerebrosides, waxes, and sterols such as cholesterol and ergosterol. Lipids which can be removed from a cancer cell include but are not limited to the removal of polar lipids, non-polar lipids, sphingolipids, cholesterol, phospholipids or a combination thereof. In one embodiment, the total concentration of lipid remaining in the modified cancer cell is less than 80% of the total concentration of lipid in the original cancer cell. In another embodiment, the total concentration of lipid remaining in the modified cancer cell is less than 50% of the total concentration of lipid in the original cancer cell. In a preferred embodiment, the total concentration of lipid remaining in the modified cancer cell is less than 30% of the total concentration of lipid in the original cancer cell. In a further embodiment, the total concentration of lipid remaining in the modified cancer cell is less than 20% of the total concentration of lipid in the original cancer cell. In a further embodiment, the total concentration of lipid remaining in the modified cancer cell is less than 10% of the total concentration of lipid in the original cancer cell. In a further embodiment, the total concentration of lipid remaining in the modified cancer cell is less than 5% of the total concentration of lipid in the original cancer cell. In another embodiment, the total concentration of lipid remaining in the modified cancer cell is between 1% and 80% of the total concentration of lipid in the original cancer cell.

Additionally, modified cancer cells and cancer cell particles may in one embodiment possess protein recovery rates in excess of 50% of the total protein content as compared to a non-delipidated cancer cell.

The terms "pharmaceutically acceptable carrier or pharmaceutically acceptable vehicle" are used herein to mean any liquid including but not limited to water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The term "patient" refers to an animal or a human.

The term "patient specific antigen" refers to an antigen that is capable of inducing a patient specific immune response when introduced into that patient. Such patient specific antigens may be cancer associated antigens or tumor associated antigens. A patient specific antigen includes any antigen, for example a cancer associated antigen.

The term "Tumor Associated Antigen (TAA) or cancer cell associated antigen refers to an antigen known to one of ordinary skill in the art as being associated with a tumor or cancer cell. Non-limiting examples of TAAs embodied by the present invention can be found in Table 1. It will be apparent to one of ordinary skill in the art that a TAA can comprise a cell surface antigen, membrane bound to a cancer cell. Many such antigens are glycosylated, for example GP-100. In another embodiment, the TAA's can also comprise intracellular cancer specific antigens. As demonstrated herein, DCs can uptake and process delipidated cancer cells. Accordingly, the present invention encompasses a method for the presentation of intracellular cancer specific antigens to the cell-mediated immune system.

TABLE 1

Tumor/Cancer Associated Antigens (TAAs) embodied by the instant application.

| | |
|---|---|
| AFP | Alpha (α)-fetoprotein |
| AIM-2 | Interferon-inducible protein absent in melanoma 2 |
| ALL | Acute lymphoblastic leukemia |
| AML | Acute myeloid leukemia |
| 707-AP | 707 alanine proline |
| APL | Acute promyelocytic leukemia |
| ART-4 | Adenocarcinoma antigen recognized by T cells 4 |
| BAGE | B antigen |
| bcr-abl | Breakpoint cluster region-Abelson |
| CAMEL | CTL-recognized antigen on melanoma |
| CAP-1 | Carcinoembryonic antigen peptide-1 |
| CASP-8 | Caspase 8 |
| CDC27 | Cell division cycle 27 |

TABLE 1-continued

Tumor/Cancer Associated Antigens (TAAs) embodied by the instant application.

| | |
|---|---|
| CDK4 | Cyclin-dependent kinase 4 |
| CEA | Carcinoembryonic antigen |
| CLCA2 | Calcium-activated chloride channel 2 |
| CML | Chronic myelogenous leukemia |
| CT | Cancer-testis (antigen) |
| CTL | Cytotoxic T lymphocytes |
| Cyp-B | Cyclophilin B |
| DAM | Differentiation antigen melanoma |
| ELF2 | Elongation factor 2 |
| Ep-CAM | Epithelial cell adhesion molecule |
| EphA2, 3 | Ephrin type-A receptor 2, 3 |
| Ets | E-26 transforming specific |
| ETV6-AML1 | Ets variant gene 6/acute myeloid leukemia 1 gene ETS |
| FGF-5 | Fibroblast growth factor 5 |
| FN | Fibronectin |
| G250 | Glycoprotein 250 |
| GAGE | G antigen |
| GnT-V | N-Acetylglucosaminyltransferase V |
| Gp100 | Glycoprotein 100 kDa |
| HAGE | Helicase antigen |
| HER-2/neu | Human epidermal receptor 2/neurological |
| HAL-A*0201-R170I | Arginine (R) to isoleucine (I) exchange at residue 170 of the α-helix of the α2-domain in the HLA-A2 gene |
| H/N | Head and neck |
| HSP70-2M | Heat shock protein 70-2 mutated |
| HST-2 | Human signet-ring tumor 2 |
| hTERT | Human telomerase reverse transcriptase |
| iCE | Intestinal carboxyl esterase |
| IL-13Rα2 | Interleukin 13 receptor α2 chain |
| KIAA0205 | Name of the gene as it appears in databases |
| LAGE | L antigen |
| LDLR/FUT | Low density lipid receptor/GDP-L-fucose: β-D-galactosidase 2-α-L-fucosyltransferase |
| MAGE | Melanoma antigen |
| MART-1/Melan-A | Melanoma antigen recognized by T cells-1/melanoma antigen A |
| MART-2 | Melanoma Ag recognized by T cells-2 |
| MCIR | Melanocortin 1 receptor |
| M-CSF | Macrophage colony-stimulating factor gene |
| MHC | Major histocompatibility complex |
| MSI | Microsatellite instability |
| MUC1, 2 | Mucin 1, 2 |
| MUM-1, -2, -3 | Melanoma ubiquitous mutated 1, 2, 3 |
| NA88-A | NA cDNA clone of patient M88 |
| Neo-PAP | Neo-poly(A) polymerase |
| NPM/ALK | Nucleophosmin/anaplastic lymphoma kinase fusion protein |
| NSCLC | Non-small cell lung carcinoma |
| NY-ESO-1 | New York esophageous 1 |
| OA1 | Ocular albinism type 1 protein |
| OGT | O-Linked N-acetylglucosamine transferase gene |
| ORF | Open reading frame |
| OS-9 | Name of the gene as it appear in databases |
| P15 | Protein 15 |
| p190 mnor bcr-abl | Protein of 190-kDa bcr-abl |
| Pml/RARα | Promyelocytic leukemia/retinoic acid receptor α |
| PRAME | Preferentially expressed antigen of melanoma |
| PSA | Prostrate-specific antigen |
| PSMA | Prostrate-specific membrane antigen |
| PTPRK | Receptor-type protein-tyrosine phosphatase kappa |
| RAGE | Renal antigen |
| RCC | Renal cell carcinoma |
| RU1, 2 | Renal ubiquitous 1, 2 |
| SAGE | Sarcoma antigen |
| SART-1, -2, -3 | Squamous antigen rejecting tumor 1, 2, 3 |
| SCC | Squamous cell carcinoma |
| SSX-2 | Synovial sarcoma, X breakpoint 2 |
| Survivin-2B | Intron 2-retaining survivin |
| SYT/SSX | Synaptotagmin I/synovial sarcoma, X fusion protein |

TABLE 1-continued

Tumor/Cancer Associated Antigens (TAAs) embodied by the instant application.

| | |
|---|---|
| TEL/AML1 | Translocation Ets-family leukemia/acute myeloid leukemia 1 |
| TGFβRII | Transforming growth factor β receptor 2 |
| TPI | Triosephosphate isomerase |
| TRAG-3 | TAxol resistant associated protein 3 |
| TRG | Testin-related gene |
| TRP-1 | Tyrosinase-related protein 1, or gp75 |
| TRP-2 | Tyrosinase-related protein 2 |
| TRP-2/INT2 | TRP-2/intron 2 |
| TRP-2/6B | TRP-2/novel exon 6b |
| TSTA | Tumor-specific transplantation antigens |
| WT1 | Wilms' tumor gene |

Methods of Manufacture of the Modified Cancer Cell

One of ordinary skill in the art would appreciate that multiple delipidation processes are encompassed within the scope of the present invention. In a preferred embodiment, a solvent system together with a mechanical mixing system is used to substantially delipidate the cancer cell. The delipidation process is dependent upon the total amount of solvent and energy input into a system. Various solvent levels and mixing methods, as described below, may be used depending upon the overall framework of the process. Practice of the method of the present invention to reduce the lipid content of a cancer cell creates a modified cancer cell or cancer cell particle. These modified cancer cell have lower levels of lipid and are immunogenic. The present methods expose or modify epitopes that are not usually presented to the immune system by untreated cancer cells. It is believed that delipidation not only exposes epitopes but also enhances the antigen processing and presentation of tumor associated antigens because of the conformational shape the antigen is presented in after delipidation. Methods of the present invention solve numerous problems encountered with prior art methods. By substantially decreasing the lipid content of the lipid envelope of the cancer cell, and keeping the modified cancer cell intact, the method of the present invention exposes or modifies additional antigens. The host immune system recognizes the modified cancer cell as foreign. Using the method of the present invention, what is created is a modified cancer cell or cancer cell particle in which additional antigens are exposed, thereby using the epitopes of the actual cancer cell to initiate a positive immunogenic response in the patient following administration.

Modified, partially delipidated cancer cells or particles obtained with some embodiments of the methods disclosed herein represent, in some aspects, new therapeutic vaccine compositions for therapeutic immunization and induction of an immune response in animals or humans. In one aspect, modified, partially delipidated cancer cell obtained with the methods disclosed herein are useful for therapeutic immunization and induction of an immune response in animals or humans afflicted with a cancer. In another embodiment, modified cancer cells obtained with the methods disclosed herein are useful for immunization of animals and humans who do not have the cancer in order to provoke an immune response when cancers may develop. In one embodiment of the present invention, administration of the modified, partially delipidated cancer cells and compositions comprising such cells provides a new method of treatment, alleviation, or containment of cancer growth, conditions or clinical symptoms associated with the cancer.

Partially delipidated cancer cells and cancer cell particles obtained according to some of aspects of the present invention possess at least some structural characteristics that distinguish them from conventional cancer cells. Such characteristics include, but are not limited to, reduced lipid content, modified protein content, or the ratio of lipid content to protein content. For example, a partially delipidated cancer cell or cancer cell particle according to some embodiments of the present invention has a lower cholesterol content than the cholesterol content of the non-delipidated cancer cell. In one embodiment, the lower cholesterol content of the partially delipidated cancer cell particle can be at least 70% to 99% lower than the cholesterol content of non-delipidated cancer cells. In other embodiments, the cholesterol content in the modified, partially delipidated cancer cell particle is reduced, for example, by about 99%, 90%, 70%, 50%, 30% or 20% as compared to the unmodified cancer cell. It is to be understood that cholesterol is but one form of lipid which may be reduced following treatment of the cancer cells, and other lipids as defined herein, or combinations of these lipids may be reduced.

Modified, partially delipidated cancer cell may also be characterized, for example, as retaining >50% of the cancer cell total protein content. In one embodiment of the present invention, the TAAs that are retained in the modified cancer cell include but are not limited to TAAs found in Table 1. In another embodiment the TAAs comprise GP 100 and TRP-2. However, it will be appreciated by one of ordinary skill in the art that the TAAs retained by the modified cancer cell will vary depending on the type of cancer present.

Exemplary Solvent Systems for Use in Removal of Lipid from Cancer Cells to Produce Delipidated Cancer Cells or Particles Useful for Vaccine Production The solvent or combinations of solvents to be employed in the process of partially or completely delipidating lipid-containing cancer cells and in producing vaccines may be any solvent or combinations thereof effective in solubilizing lipids while retaining antigen components of the cancer cell, which can be measured in one embodiment, via protein recovery. This delipidation process that keeps antigen components of the cancer cell intact is a matter of defining the right solvent-energy systems. Suitable solvents comprise hydrocarbons, ethers, alcohols, phenols, esters, halohydrocarbons, halocarbons, amines, and mixtures thereof. Aromatic, aliphatic, or alicyclic hydrocarbons may also be used. Other suitable solvents, which may be used with the present invention, include amines and mixtures of amines. A preferred solvent combination comprises alcohols and ethers. One solvent system is DIPE, either concentrated or diluted in water or a buffer such as a physiologically acceptable buffer. One solvent combination comprises alcohols and ethers. Another preferred solvent comprises ether or combinations of ethers, either in the form of asymmetrical ethers or halogenated ethers.

The optimal solvent systems are those that accomplish two objectives: first, at least partially delipidating the cancer cell and second, providing few or no deleterious effects on the antigenic proteins of the cancer cells. In addition, the solvent system should maintain the integrity of the cancer cell particle such that it can be used to initiate an immune response in the patient. It should therefore be noted that certain solvents, solvent combinations, and solvent concentrations may be too harsh to use in the present invention because they result in unacceptable degradation of cancer cell proteins.

It is preferred that the solvent or combination of solvents has a relatively low boiling point to facilitate removal through a vacuum and possibly heat without destroying the antigens of the cancer cell. It is also preferred that the solvent or combination of solvents be employed at a low temperature because heat may have deleterious effects on proteins. It is also preferred that the solvent or combination of solvents at least partially delipidate the cancer cell.

Removal of solvents from delipidated cancer cells may be accomplished through use of a second extraction solvent or a de-emulsifying agent. For example, demulsifying agents such as ethers may be used to remove a first solvent such as an alcohol from an emulsion. Removal of solvents may also be accomplished through other methods, which do not employ additional solvents, including but not limited to the use of charcoal. Charcoal may be used in a slurry or alternatively, in a column to which a mixture is applied. Charcoal is a preferred method of removing solvents. Pervaporation may also be employed to remove one or more solvents from delipidated cancer cell mixtures.

Examples of suitable amines for use in removal of lipid from lipid-containing cancer cells in the present invention are those which are substantially immiscible in water. Typical amines are aliphatic amines—those having a carbon chain of at least 6 carbon atoms. A non-limiting example of such an amine is $C_6H_{13}NH_2$.

The preferred alcohols for use in the present invention, when used alone, include those alcohols that are not appreciably miscible with plasma or other biological fluids. Such alcohols include, but are not limited to, straight chain and branched chain alcohols, including pentanols, hexanols, heptanols, octanols and those alcohols containing higher numbers of carbons. Alcohols may be used alone or in combination with another solvent, for example an ether. Concentrations of alcohols may be employed to remove lipids when used alone and not in combination with other solvents. For example, a concentration range of alcohols include 0.1% to 99.9%. For example, concentrations of alcohols that may be employed include, but are not limited to the following: 0.1%, 1.0%, 2.5%, 5%, 10.0% and 25% or higher.

When alcohols are used in combination with another solvent, for example, an ether, a hydrocarbon, an amine, or a combination thereof, $C_1$-$C_8$ containing alcohols may be used. Preferred alcohols for use in combination with another solvent include $C_4$-$C_8$ containing alcohols. Accordingly, preferred alcohols that fall within the scope of the present invention are butanols, pentanols, hexanols, heptanols and octanols, and iso forms thereof. In particular, $C_4$ alcohols or butanols (1-butanol and 2-butanol) are preferred. The specific alcohol choice is dependent on the second solvent employed. In a preferred embodiment, lower alcohols are combined with lower ethers.

Ether, when used either alone or in combination with other solvents (preferably alcohols), is another preferred solvent for use in the method of the present invention. Particularly preferred are the $C_4$-$C_8$ containing-ethers, including but not limited to ethyl ether, diethyl ether, and propyl ethers (including but not limited to di-isopropyl ether (DIPE)). Asymmetrical ethers may also be employed. Halogenated symmetrical and asymmetrical ethers may also be employed.

Low concentrations of solvents, such as ethers, may be employed to remove lipids when used alone and not in combination with other solvents. For example, a low concentration range of ethers include 0.5% to 30%. For example, concentrations of ethers that may be employed include, but are not limited to the following: 0.625%, 1.0% 1.25%, 2.5%, 3%, 5.0% and 10% or higher. It has been observed that dilute solutions of ethers are effective to remove lipids from cells. Such solutions may be aqueous solutions or solutions in aqueous buffers, such as phosphate buffered saline (PBS). Other physiological buffers may be used, including but not limited to bicarbonate, citrate, Tris, Tris/EDTA, and Trizma. Preferred ethers are di-isopropyl ether (DIPE) and diethyl ether (DEE). Ethers may also be used in combination in the present invention—such as a solvent mixture of DIPE and DEE. Low concentrations of ethers may also be used in combination with alcohols, for example, n-butanol.

When ethers and alcohols are used in combination as a first solvent for removing lipid from lipid-containing cancer cells, any combination of alcohol and ether may be used provided the combination is effective to at least partially remove lipid from the cancer cell, without having deleterious effect on the immunogenic proteins. When alcohols and ether are combined as a first solvent for treating the cancer cells contained in a fluid, useful ratios of alcohol to ether in this solvent range from about 0.01 parts alcohol to 99.99 parts ether to 60 parts alcohol to 40 parts ether, with a specific ratio range of about 10 parts alcohol to 90 parts ether to 5 parts alcohol to 95 parts ether, with a specific ratio range of about 10 parts alcohol to 90 parts ether to 50 parts alcohol to 50 parts ether, with a specific ratio range of about 20 parts alcohol to 80 parts ether to 45 parts alcohol to 55 parts ether, with a specific range of about 25 parts alcohol to 75 parts ether with respect to each other. In one embodiment, the ratio of alcohol to ether is 1 part alcohol, to 1 part ether and 98 parts fluid containing the cancer cells.

An especially preferred combination of alcohol and ether is the combination of butanol and DIPE. When butanol and DIPE are combined as a first solvent for treating cancers contained in a fluid, useful ratios of butanol to DIPE in this solvent are about 0.01 parts butanol to 99.99 parts DIPE to 60 parts butanol to 40 parts DIPE, with a specific ratio range of about 10 parts butanol to 90 parts DIPE to 5 parts butanol to 95 parts DIPE, with a specific ratio range of about 10 parts butanol to 90 parts DIPE to 50 parts butanol to 50 parts DIPE, with a specific ratio range of about 20 parts butanol to 80 parts DIPE to 45 parts butanol to 55 parts DIPE, with a specific range of about 25 parts butanol to 75 parts DIPE with respect to each other. In another embodiment, a ratio range of combined solvent to tumor cell containing fluid are about 0.5 parts combined solvent to 99.5 parts tumor cell containing fluid to 2 parts combined solvent to 1 part cancer cell containing fluid.

Another combination of alcohol and ether is the combination of butanol with DEE. When butanol is used in combination with DEE as a first solvent, useful ratios of butanol to DEE are about 0.01 parts butanol to 99.99 parts DEE to 60 parts butanol to 40 parts DEE, with a specific ratio range of about 10 parts butanol to 90 parts DEE to 5 parts butanol to 95 parts DEE with a specific ratio range of about 10 parts butanol to 90 parts DEE to 50 parts butanol to 50 parts DEE, with a specific ratio range of about 20 parts butanol to 80 parts DEE to 45 parts butanol to 55 parts DEE, with a specific range of about 40 parts butanol to 60 parts DEE.

Additionally, when employing a solvent containing n-butanol, the present invention can also use a ratio of solvent that yields about 0.1%-5% n-butanol in the final solvent/ cancer cell suspension, for example, 0.1%, 0.5%, 1%, 2%, 3%, 4% or 5% n-butanol may be used.

Liquid hydrocarbons dissolve compounds of low polarity such as the lipids found in the cancer cells. Particularly effective in disrupting the lipid membrane of a cancer cell are hydrocarbons which are substantially water immiscible and liquid at about 37° C. Suitable hydrocarbons include, but are not limited to the following: $C_5$ to $C_{20}$ aliphatic hydrocarbons such as petroleum ether, hexane, heptane, octane; haloaliphatic hydrocarbons such as chloroform, 1,1,2-trichloro-1,2,2-trifluoroethane, 1,1,1-trichloroethane, trichloroethylene, tetrachloroethylene, dichloromethane and carbon tetrachloride; thioaliphatic hydrocarbons each of which may be linear, branched or cyclic, saturated or unsaturated; aromatic hydrocarbons such as benzene; alkylarenes such as toluene; haloarenes; haloalkylarenes; and thioarenes. Other suitable solvents may also include saturated or unsaturated heterocyclic compounds such as pyridine and aliphatic, thio- or halo-derivatives thereof.

Suitable esters for use in the present invention include, but are not limited to, ethyl acetate, propylacetate, butylacetate and ethylpropionate. Suitable detergents/surfactants that may be used include but are not limited to the following: sulfates, sulfonates, phosphates (including phospholipids), carboxylates, and sulfosuccinates. Some anionic amphiphilic materials useful with the present invention include but are not limited to the following: sodium dodecyl sulfate (SDS), sodium decyl sulfate, bis-(2-ethylhexyl) sodium sulfosuccinate (AOT), cholesterol sulfate and sodium laurate.

Cancer Cells and Treatment Thereof for Producing Exposed Cancer Cell-Associated Antigens As stated above, various cancers may be treated with the method of the present invention in order to expose cancer cell-associated antigens of the cancer cells. In a preferred embodiment, cancer samples obtained from an animal or human are treated with the method of the present invention in order to remove lipid and expose or modify cancer cell-associated antigens. In this embodiment, cancer samples such as biopsies may be obtained from an animal or human patient by any conventional means, including various surgical techniques and treating the sample in order to isolate the cancer cells. Some cancer cells may be obtained from fluids such as plasma, peritoneal, pleural, pericardial and cerebrospinal fluids. Such methods for excising and isolating cancer cells are known to one of ordinary skill in the art.

Once a cancer cell is obtained either in this manner, or for example, from a storage facility housing samples of cancer cells, the cancer cell is contacted with a first organic solvent, as described above, capable of solubilizing lipid in the cancer cell. The first organic solvent is combined with the cancer cells or a medium containing the cancer cells in a ratio wherein the first solvent is present in an amount effective to substantially solubilize the lipid in the cancer cells, for example, dissolve the lipid envelope that surrounds the cells. Acceptable ratios of first solvent to medium (expressed as a ratio of first organic solvent to the medium containing the cancer cells) are described in the following ranges: 0.5-4.0:0.5-4.0; 0.8-3.0:0.8-3.0; and 1-2:0.8-1.5. Various other ratios may be applied, depending on the nature of the medium and concentration of the cancer cells in that medium. For example, in the case of cell culture fluid, the following ranges may be employed of first organic solvent to cell culture fluid: 0.5-4.0:0.5-4.0; 0.8-3.0:0.8-3.0; and 1-2:0.8-1.5.

After contacting the medium containing the cancer cells with the first solvent as described above, the first solvent and medium are mixed using a method that includes, but is not limited to, any one of the following suitable mixing methods: gentle stirring; vigorous stirring; vortexing; swirling; shaking, homogenization; and end-over-end rotation. In one embodiment, the first solvent and medium are mixed using end-over-end rotation. In another embodiment, the first solvent and medium are mixed by shaking.

The amount of time required for adequate mixing of the first solvent with the medium is related to the mixing method employed. Medium is mixed for a period of time sufficient to permit intimate contact between the organic and aqueous phases, and for the first solvent to at least partially or completely solubilize the lipid contained in the cancer cells. Typically, mixing will occur for periods of about 5 seconds to about 24 hours, 10 seconds to about 2 hours, approximately 10 seconds to approximately 10 minutes, or about 30 seconds to about 1 hour, depending on the mixing method employed and the quantity of the cells being treated. Non-limiting examples of mixing durations associated with different methods are presented in the next sentences. Gentle stirring and end-over-end rotation may occur for a period of about 5 seconds to about 24 hours. Vigorous stirring and vortexing may occur for a period of about 5 seconds to about 30 minutes. Swirling may occur for a period of about 5 seconds to about 2 hours. Homogenization may occur for a period of about 5 seconds to about 10 minutes. Shaking may occur for a period of about 5 seconds to about 2 hours.

Separation of Solvents

After mixing the first solvent with the medium, the solvent is separated from the medium being treated. The organic and aqueous phases may be separated by any suitable manner known to one of ordinary skill in the art. Since the first solvent is typically immiscible in the aqueous fluid, the two layers are permitted to separate and the undesired layer is removed. The undesired layer is the solvent layer containing dissolved lipids and its identification, as known to one of ordinary skill in the art, depends on whether the solvent is more or less dense than the aqueous phase. An advantage of separation in this manner is that dissolved lipids in the solvent layer may be removed.

In addition, separation may be achieved through means, including but not limited to the following: removing the undesired layer via pipetting; centrifugation followed by removal of the layer to be separated; creating a path or hole in the bottom of the tube containing the layers and permitting the lower layer to pass through; utilization of a container with valves or ports located at specific lengths along the long axis of the container to facilitate access to and removal of specific layers; and any other means known to one of ordinary skill in the art. Another method of separating the layers, especially when the solvent layer is volatile, is through distillation under reduced pressure or evaporation at room temperature, optionally combined with mild heating. In one embodiment employing centrifugation, relatively low g forces are employed, such as 900×g for about 5 to 15 minutes to separate the phases.

A preferred method of removing solvent is through the use of charcoal, preferably activated charcoal. This charcoal is optionally contained in a column. Alternatively the charcoal may be used in slurry form. Various biocompatible forms of charcoal may be used in these columns. Pervaporation methods and use of charcoal to remove solvents are preferred methods for removing solvent.

Following separation of the first solvent from the treated medium, some of the first solvent may remain entrapped in the aqueous layer as an emulsion. Optionally, a de-emulsifying agent is employed to facilitate removal of the trapped first solvent. Still another method of removing solvent is the use of hollow fiber contactors. The de-emulsifying agent may be any agent effective to facilitate removal of the first solvent. A preferred de-emulsifying agent is ether and a more preferred de-emulsifying agent is diethyl ether. The de-emulsifying agent may be added to the fluid or in the alternative the fluid may be dispersed in the de-emulsifying agent. In vaccine preparation, alkanes in a ratio of about 0.5 to 4.0 to about 1 part of emulsion (vol:vol) may be employed as a demulsifying agent, followed by washing to remove the residual alkane from the remaining delipidated cancer cell used for preparing the vaccine. Preferred alkanes include, but are not limited to, pentane, hexane and higher order straight and branched chain alkanes.

The de-emulsifying agent, such as ether, may be removed through means known to one of skill in the art, including such means as described in the previous paragraph. One convenient method to remove the de-emulsifying agent, such as ether, from the system, is to permit the ether to evaporate from the system in a running fume hood or other suitable device for collecting and removing the de-emulsifying agent from the environment. In addition, de-emulsifying agents may be removed through application of higher temperatures, for example from about 24 to 37° C. with or without pressures of about 10 to 20 mbar. Another method to remove the de-emulsifying agent involves separation by centrifugation, followed by removal of organic solvent through aspiration, further followed by evaporation under reduced pressure (for example 50 mbar) or further supply of an inert gas, such as nitrogen, over the meniscus to aid in evaporation.

Cancer cells or fragments of cancer cells treated with the delipidation method of the present invention may be collected or concentrated using methods known to one of ordinary skill in the art. Such methods include but are not limited to the following, centrifugation, filtration, sieving, cell sorting and chromatography, for example affinity chromatography.

Methods of Treating Biological Fluids Containing Cancer Cells (Delipidation)

It is to be understood that the method of the present invention is employed in either a continuous or discontinuous manner. In a discontinuous or batch mode of operation, the present invention employs a cancer tissue sample or dispersed cells previously obtained from a human or animal. The sample is treated with the method of the present invention to produce a new sample which contains at least partially or completely delipidated cancer cells, or modified cancer cells. One embodiment of this mode of the present invention is to treat cancer cell samples previously obtained from animals or humans and stored in a cell bank for subsequent use to create DC-cancer cell hybrids. These samples may be administered with the method of the present invention to eliminate cancers or minimize the proliferation of a cancer.

Delipidation of cancer cells can be achieved by various means. A batch method can be used for fresh or stored cancer cells. In this case a variety of the described organic solvents or mixtures thereof can be used for cancer cell delipidation. Extraction time depends on the solvent or mixture thereof and the mixing procedure employed.

Through the use of the methods of the present invention, levels of lipid in lipid-containing cancer cells are reduced, and the fluid, for example, containing the delipidated cancer cell particles may be administered to the patient. Such fluid containing modified cancer cell particles may act as a vaccine and provide protection in the patient against the cancer or provide a treatment in a patient afflicted with the cancer by generating an immune response and decreasing the severity of the cancer. These modified cancer particles induce an immune response in the recipient to exposed epitopes on the modified cancer cell particles. Alternatively the modified cancer cell particles may be combined with a pharmaceutically acceptable carrier, and optionally an adjuvant, and administered as a vaccine composition to a human or an animal to induce an immune response in the recipient.

Vaccine Production—Embodiment One

The modified cancer cell, which is at least partially or substantially delipidated and has exposed tumor associated antigens, has immunogenic properties and is combined with a pharmaceutically acceptable carrier to make a composition comprising a vaccine. This vaccine composition is optionally combined with an adjuvant or an immunostimulant and administered to an animal or a human. Both autologous and non-autologous vaccines, including combination vaccines, are within the scope of the present invention. It is to be understood that vaccine compositions may contain more than one type of modified cancer cell or component thereof, in order to provide protection against complex cancers. Such combinations may be selected according to the desired immunity.

Vaccine Production Employing Dendritic Cells and Delipidated Cancer Cells—Embodiment Two Dendritic cells can be used to induce an antitumoral response within a patient. Dendritic cells are hematopoietically derived leucocytes that form a cellular network involved in immune surveillance, antigen capture, and antigen presentation. There are numerous techniques for isolating and propagating DCs in vitro known to one of ordinary skill in the art (see: M. B. Lutz et al. J. Imm. Methods 223 (1999) 9277-9279) and, therefore, they can be used in immunization strategies. To date, DCs together with synthetic peptides having known cancer antigens, stripped peptides derived from class I molecules, tumor RNA, or tumor lysates have been used to improve the immunogenic response of patients to cancer.

In one embodiment, tumor tissue is removed, delipidated in accordance with the above-described invention, placed in phosphate-buffered saline (PBS), and used to produce a single-cell suspension. Cells are lysed using techniques known to one of ordinary skill in the art, for example by multiple freeze cycles, such as three to five, in liquid nitrogen and thaw cycles at room temperature. Lysis is preferably monitored. Large particles are removed by centrifugation and supernatants are passed through a filter. The protein contents are determined and stored for future use. The objective of this lysis step is to produce antigenic components that are exposed via the delipidation process.

After generating dendritic cells from peripheral blood, in accordance with methods known to those of ordinary skill in the art, the dendritic cells are cultured, i.e., for about 7 days, and then further cultured with keyhole limpet hemocyanin (KLH) and the cancer cell lysate. One of ordinary skill in the art would recognize that the relative amounts of KLH, tumor lysate, and DCs is dependent upon, and relative to, the kind of tumor to be treated. The resultant cells are washed with PBS and then resuspended in RPMI-1640 for use in treatment. In one embodiment, the cell vaccine preparation is prepared in a solution suitable for administration to humans, such as, but not limited to, saline, PBS or other approved solutions. This process creates a DC-cancer cell hybrid.

It is to be understood that other molecules besides KLH may be used, for example, thyroglobulin or serum albumin, as commonly known to one of ordinary skill in the art.

Administration of Vaccine of Embodiment One, Produced with the Method of the Present Invention When a delipidated cancer cell is administered to an animal or a human, it is typically combined with a pharmaceutically acceptable carrier to produce a vaccine, and optionally combined with an adjuvant or an immunostimulant as known to one of ordinary skill in the art. The vaccine formulations may conveniently be presented in unit dosage form and may be prepared by conventional pharmaceutical techniques known to one of ordinary skill in the art. Such techniques include uniformly and intimately bringing into association the active ingredient and the liquid carriers (pharmaceutical carrier(s) or excipient(s)). Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers—for example, sealed ampules and vials—and may be stored in a freeze-dried (lyophilized) condition requiring only the addition of the sterile liquid carrier, for example, water for injections, immediately prior to use. The vaccine may be stored at temperatures of from about 4° C. to −100° C. The vaccine may also be stored in a lyophilized state at different temperatures including room temperature. Extemporaneous injection solutions and suspensions may be prepared from sterile powders, granules and tablets commonly used by one of ordinary skill in the art. The vaccine may be sterilized through conventional means known to one of ordinary skill in the art. Such means include, but are not limited to filtration, radiation and heat. The vaccine of the present invention may also be combined with bacteriostatic agents, such as thimerosal, to inhibit bacterial growth.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The vaccine may be administered through different routes, such as oral, including buccal and sublingual, rectal, parenteral, aerosol, nasal, intramuscular, subcutaneous, intradermal, intravenous, intraperitoneal, and topical. The vaccine may also be administered in the vicinity of lymphatic tissue, for example through administration to the lymph nodes such as axillary, inguinal or cervical lymph nodes, or through the lymphatic tissue of the gut (GALT).

The vaccine of the present invention may be administered in different forms, including but not limited to solutions, emulsions and suspensions, microspheres, particles, microparticles, nanoparticles, and liposomes. It is expected that from about 1 to 5 dosages may be required per immunization regimen. Initial injections may range from about 1 ng to 1 gram, from about 0.1 mg to 800 mg, and from approximately 1 mg to 500 mg. Booster injections may range from 1 ng to 1 gram, from approximately 0.1 mg to 750 mg, and from about 0.5 mg to 500 mg. The volume of administration will vary depending on the administration route. Intramuscular injections may range from about 0.01 ml to 1.0 ml.

One of ordinary skill in the medical or veterinary arts of administering vaccines will be familiar with the amount of vaccine to be administered in an initial injection and in booster injections, if required, taking into consideration, for example, the age and size of a patient. Initial injections may range from about less than 1 ng to 1 gram based on total cancer cell protein. A non-limiting range may be 1 ml to 10 ml. The volume of administration may vary depending on the administration route.

The vaccines of the present invention may be administered after detecting cancer. The vaccine of the present invention may be administered to either humans or animals. In one embodiment, the proliferation of a cancer may be reduced by introducing delipidated cancer cells. In another embodiment, the size of the cancer is actually reduced by introducing delipidated cancer cells.

In another embodiment, the vaccines of the present invention may be administered to an individual without cancer or at high risk of developing cancer in order to prevent or delay the onset of cancer. For example, women with mothers and/or grandmothers who had ovarian cancer and/or breast cancer are more likely to develop ovarian cancer or breast cancer. Other sex-linked cancers are known to one of ordinary skill in the art, and oncologists routinely advise patients that they may be more likely to develop cancer based on family history, or the interaction of family history and predisposing environmental or life style factors. Administration of the vaccines of the present invention, for example a vaccine against ovarian cancer, to an individual at risk of developing ovarian cancer, delays or prevents the occurrence of ovarian cancer in that individual.

Administration of Vaccine of Embodiment Two, Produced with the Method of the Present Invention After generating the DC-cancer lysates, as described above, it is typically combined with a pharmaceutically acceptable carrier to produce a vaccine, and optionally combined with an adjuvant or an immunostimulant as known to one of ordinary skill in the art. The vaccine formulations may conveniently be presented in unit dosage form and may be prepared by conventional pharmaceutical techniques known to one of ordinary skill in the art. Such techniques include uniformly and intimately bringing into association the active ingredient and the liquid carriers (pharmaceutical carrier(s) or excipient(s)). Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

One preferred approach to administering DC therapy includes intradermal administration or administration directly into lymph nodes. In one exemplary embodiment, patients receive the DCs pulsed with autologous cancer lysate every 3 weeks for a minimum of one and a maximum of 10 immunizations. For example, patients receive four vaccinations at 3 week intervals. Immunizations continue depending upon clinical response. In one embodiment, dendritic cells injected per vaccination range from $10 \times 10^5$ to $32 \times 10^6$ cells. However, it will be appreciated by one of ordinary skill in the art that the number of cells is variable depending on the type of cancer and immunity required. Patients are monitored for toxicities and other clinical responses.

Adjuvants

A variety of adjuvants known to one of ordinary skill in the art may be administered as part of the vaccine compositions. Such adjuvants include, but are not limited to the following: polymers, co-polymers such as polyoxyethylene-polyoxypropylene copolymers, including block co-polymers; polymer P1005; monotide ISA72; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; water-in-oil mixtures, water-in-oil-in-water mixtures or combinations thereof.

Suspending Fluids and Carriers

A variety of suspending fluids or carriers known to one of ordinary skill in the art may be employed to suspend the vaccine compositions. Such fluids include without limitation: sterile water, saline, buffer, or complex fluids derived from growth medium or other biological fluids. Preservatives, stabilizers and antibiotics known to one of ordinary skill in the art may be employed in the vaccine composition.

The following references are incorporated herein by reference in their entirety: Jocham et al., Lancet 2004: 363, 594-599; Rosenberg, N. E. Journ. Med. 2004: 350, 14-1461-1463; Yamanaka et al., Brit. J. Cancer 2003: 89, 1172-1179; Brossart, Transfusion & Apheresis Sci. 2002: 27, 183-186; O'Rourke et al., Cancer Immunol. Immunother. 2003: 52, 387-395; Lotem et al., Brit. J. Cancer 2994: 90, 773-780; Hersey et al., Cancer Immunol. Immunother. 2004: 53, 125-134; Limuna et al., J. Clin. Invest. 2004: 113, 1307-1317.

The following experimental examples are illustrative in showing that a delipidation process of cancer cells occurred and in particular, that the cancer cell was modified and noted to exhibit a positive immunogenic response in the species from which it was derived. It will be appreciated that other embodiments and uses will be apparent to those skilled in the art and that the invention is not limited to these specific illustrative examples or preferred embodiments.

EXAMPLE 1

Delipidation Protocol

Delipidation of cancer cells can be achieved as follows. Cancer cells shown in Table 2, for example at approximately $8 \times 10^5$ cells in phosphate buffered saline (PBS) were added to a final volume of 0.05% Triton X-100 plus 3% diisopropylether (DIPE). The cancer cells were resuspended in 1 ml saline. 0.05% Triton X-100 and DIPE was added to a final concentration of 3%. DIPE was added as 100% (30 μl of neat DIPE) to the cancer cell suspension and 5 μl of neat (100%) Triton was also added to make a final volume of 1 mL cancer cell suspension. The solvent mixture can also be made independently and then added to the cancer cell suspension. The cancer cell suspension was mixed end-over-end at room temperature for 20 minutes. The sample was subsequently centrifuged at 1000 rpm for 1 minute. Residual solvents were removed through a charcoal column. Following the solvent removal step the cell suspension was diluted to a final volume of 2.5 ml. An aliquot of the resuspended pellet was used to detect total cholesterol or total protein content to confirm delipidation of the cancer cells, as described below.

It will be readily apparent to one of ordinary skill in the art, that the above procedure can be modified depending on the scale of the delipidation. For example, in a large scale delipidation procedure or perhaps in a different solvent to cell suspension ratio, the bulk solvent layer can be removed and the residual solvents are either absorbed through the use of charcoal or removed via centrifugation.

EXAMPLE 2

Total Cholesterol and Total Protein Content

An aliquot of the resuspension solution from Example 1 was used in a total cholesterol assay. A further aliquot of the resuspension solution from Example 1 was used in a total protein assay using commercially available kits. For example, 50 μl of the resuspension solution from Example 1 was used in a Amplex Red Total Cholesterol Assay (Molecular Probes, Eugene, Oreg.). Another 50 μl of the resuspension solution was used in a total protein assay using the BioRad Total Protein Assay (Bio-Rad Laboratories, Hercules, Calif.). The results from these studies are presented in Table 3 which demonstrates that all delipidated cancer cell lines, regardless of source, were successfully delipidated as observed by the reduction in cholesterol concentration. Clearly, the 3% DIPE-0.05% triton X-100 protocol described in Example 1 efficiently removes lipids from a variety of cancer cells, including the murine cancer cell line B16-F10. Table 3 demonstrates >99% depletion of cholesterol, while retaining >50% protein. Clearly, B16-F10 and TF-1 cell lines were delipidated very efficiently. In addition, it appears the cell structure is maintained because of the good protein recovery rates achieved.

TABLE 2

| Cell Line | Source | Description |
| --- | --- | --- |
| TF-1 | Human | Erythroleukemia cell line |
| MT-2 | Human | CD4 T-cell line |
| CEMx174 | Human | CD4 T-cell/B-cell line |
| JAWS-II | Murine-C57BL/6 | Immature dendritic cell line |
| B16-F10 | Murine-C57BL/6 | Melanoma cell line |

TABLE 3

| | CELL LINE | PROTEIN CONCENTRATION (ug/ml) | | CHOLESTEROL CONCENTRATION (ug/ml) | |
| --- | --- | --- | --- | --- | --- |
| undelipidated | TF-1 | 125.3 | 78% protein recovery | 8.36 | 97% cholesterol removal |
| delipidated | | 98.3 | | 0.28 | |
| undelipidated | MT-2 | 108.8 | 33% protein recovery | 4.09 | >99% cholesterol removal |
| delipidated | | 36.1 | | 0 | |

TABLE 3-continued

| | CELL LINE | PROTEIN CONCENTRATION (ug/ml) | | CHOLESTEROL CONCENTRATION (ug/ml) |
|---|---|---|---|---|
| undelipidated | CEMX174 | 100.8 | 34% protein recovery | 4.54 | >99% cholesterol removal |
| delipidated | | 34 | | 0 | |
| undelipidated | JAWS-II | 138.8 | 21% protein recovery | 12.76 | 93% cholesterol removal |
| delipidated | | 29.6 | | 0.83 | |
| undelipidated | B16-F10 | 118.7 | 50% protein recovery | 6.05 | 99% cholesterol removal |
| delipidated | | 68.7 | | 0.06 | |

EXAMPLE 3

Immature Dendritic Cell Uptake

Immature dendritic cells (DC) are classical antigen presenting cells (APC). These DCs efficiently take up whole pathogens, process cancer cells/antigens, and present epitopes to B-cells for antibody production, and to T-cells for cell mediated immune responses. In this experiment, immature DCs were labeled with a dye ("A" in FIG. 1) that reads in the fluorescein isothiocyanate (FITC) channel of a fluorescence-activated cell sorter (FACS) machine. Delipidated B16-F10 melanomas were labeled with a separate dye ("C" in FIG. 1) that reads in the phycoerythrin (PE) channel of the FACS machine. Accordingly, if delipidated B16-F10 cells are taken up by DCs, then fluorescence of the B16-F10 cells will decrease, while DC fluorescence will remain intact.

The dendritic cell uptake protocol briefly comprised labeling delipidated B16-F10 cells using the PKH26-GL (Red Dye Sigma-PE), incubated with immature JAWS-II cells labeled with PKH67-GL (Green Dye Sigma-FITC), at a 1:1 ratio ($1 \times 10^7 : 1 \times 10^7$). After a 24 hour incubation, flow cytometric analysis was performed, and phagocytosis was defined by the number of double-positive cells.

In order to stain at final concentrations of $2 \times 10^{-6}$ M PKH26 dye and $1 \times 10^7$ cells/ml in a 2 ml volume, the following steps were performed using aseptic techniques:

1. Adherent or bound cells were first removed using proteolytic enzymes (i.e., trypsin/EDTA) to form a single cell suspension.

2. All steps were performed at 25° C. A total of approximately $2 \times 10^7$ single cells were placed in a conical bottom polypropylene tube and washed once using medium without serum.

3. The cells were centrifuged (400×g) for 5 minutes into a loose pellet.

4. After centrifugation, the supernatant was carefully aspirated leaving no more than 25 μl of supernatant on the pellet.

5. 1 ml of Diluent C (supplied with the staining kit) was added and the solution (PKH67-GL (Green Fluorescent Cell Linking Dye, and PKH-GL (Red Fluorescent Cell Linking Dye), Sigma, St. Louis, Mo.) resuspended by pipetting to insure complete dispersion.

6. Immediately prior to staining, $4 \times 10^{-6}$ M PKH26 dye was prepared (as a 2× stock) in polypropylene tubes using Diluent C To minimize ethanol effects, the amount of dye added is less than 1% of the individual sample volume. If a greater dilution of the dye stock is necessary, an intermediate stock is made by diluting with 100% ethanol. The preparation remains at room temperature (25° C.).

7. 1 ml of cells ($2 \times 10^7$) was rapidly added to the 1 ml of PKH26 dye ($1 \times 10^7$ cells/ml). The sample was mixed by pipetting.

8. The solution was incubated at 25° C. for 2 to 5 minutes. Periodically, the tube was gently inverted to assure mixing during this staining period at 25° C.

9. To stop the staining reaction, an equal volume of serum or compatible protein solution (i.e., 1% BSA) was added and incubated for 1 min.

10. The serum-stopped sample was diluted with an equal volume of complete medium.

11. The cells were centrifuged at 400×g for 10 minutes at 25° C. to remove cells from the staining solution.

12. The supernatant was removed and the cell pellet transferred to a new tube for further washing.

13. 10 ml of complete medium was added to wash the cells, that were then centrifuged and resuspended to the desired concentration.

Figure 2:
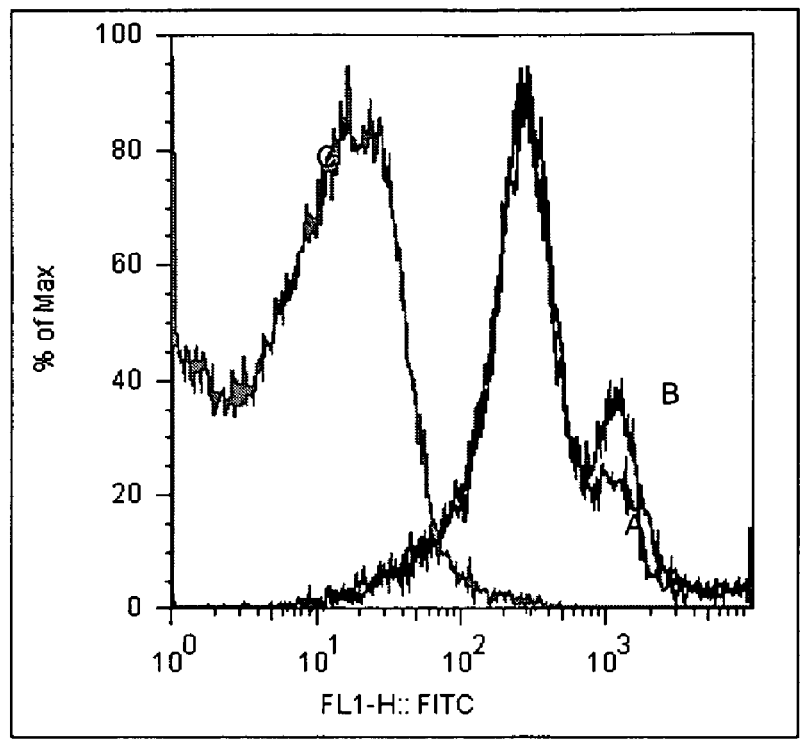
FIG. 2 depicts uptake of delipidated B16-F10 cancer cells by immature dendritic cells as determined by FACS (fluorescein isothiocyanate) (FITC) labeled.

FIGS. 1 and 2 illustrate that DCs efficiently take up delipidated B16-F10 cells.

EXAMPLE 4

In Vivo Studies—Therapeutic Vaccination

To test whether the efficient uptake of B16-F10 cells by DCs observed in Example 3 resulted in any therapeutic vaccination benefit, mice with B16 cancers were vaccinated once with autologous DC pulsed with delipidated B16-F10 cells.

Briefly, dendritic cell pulsing comprised pulsing $1 \times 10^6$ immature bone marrow derived dendritic cells (BMDDC) with $1 \times 10^6$ delipidated B16-F10 cells and 100 ng/ml Lipid A for 24 hours. The cells were incubated for an additional 24 hrs prior to adding Lipid A. The matured cells were fed with GM-CSF and Lipid A by removing 2 ml of media and adding back 2 ml media of containing GM-CSF (10 ng/ml murine GM-CSF) and Lipid A.

Cancer antigen preparation required that the cancer cells to be utilized, for example B16-F10 cells, consisted of B16-F10 cells that were delipidated using the method of the instant invention, for example a solvent mixture of 3% DIPE and 0.05% Triton X-100.

Figure 11:
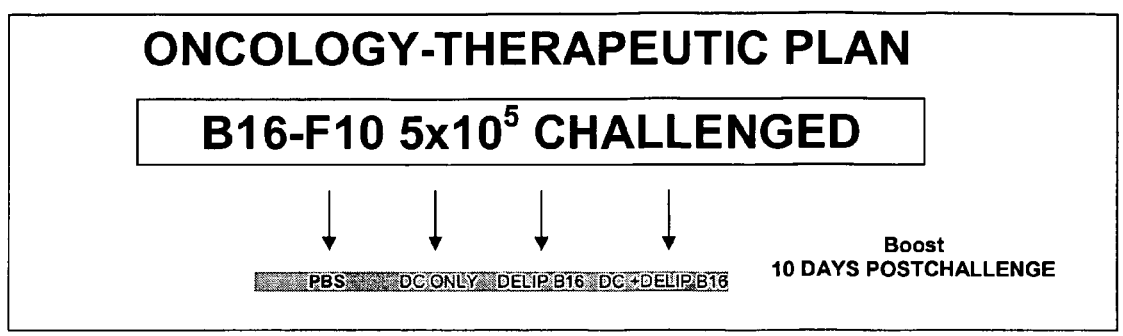
FIG. 11 is a schematic of the therapeutic vaccination experimental plan.

Mice were first challenged by injecting $2 \times 10^5$ B16-F10 cells (50 μl) in PBS subcutaneously. In Vivo mice inoculations were then performed using the following test groups (5 mice per group): A. mice unimmunized (PBS); B. mice immunized with $2 \times 10^5$ BMDDC only; C. mice immunized with $2 \times 10^5$ delipidated B16-F10 only; D. mice immunized with BMDDC pulsed with delipidated B16-F10 cells. The experimental plan is shown in FIG. 11.

Figure 3:
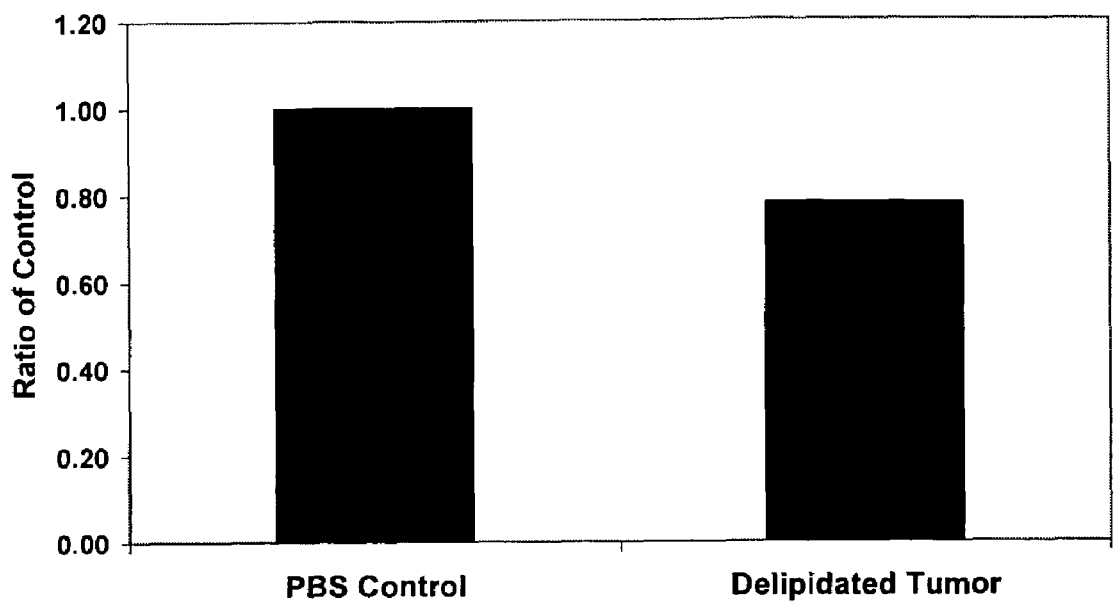
FIG. 3 depicts therapeutic vaccination and reduction of cancer growth.
Figure 4:
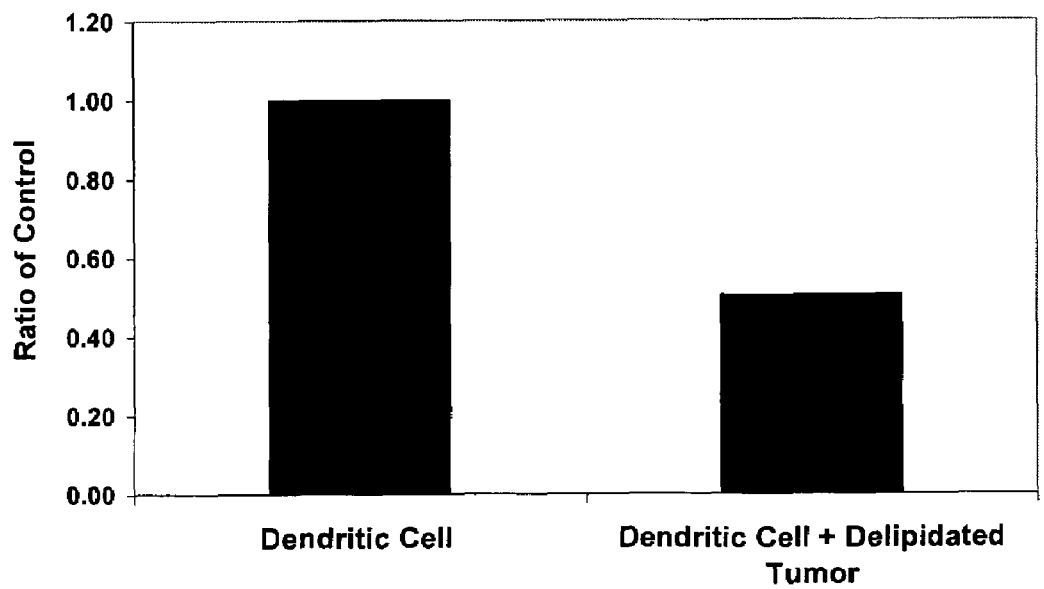
FIG. 4 is similar to FIG. 3 and depicts therapeutic vaccination using DCs pulsed with delipidated B16-F10 cancer cells.

The experimental objective was to present a therapeutic cancer model. Many cancer patients have a pre-existing cancer, and one goal is to contain cancer growth and therefore enhance the patients' survival. FIGS. 3 and 4 illustrate that, after just one boost of the vaccine, a containment of cancer growth was observed in the vaccinated group, compared to the control group. In the experiment described above, the control group was vaccinated with autologous DCs only. We believe this control group is more accurate than using a PBS control Group, since vaccinated DCs could potentially take up autologous cancer cells and enhance an immune response against the cancer. An important feature of the experiment is that the results were observed after just one vaccination cycle. Many vaccination procedures require multiple rounds of vaccination to produce an immune response. Although vaccination with delipidated B16-F10 cells reduced cancer growth compared to the PBS Control (FIG. 3), the reduction is not as drastic as when mice were vaccinated with DC pulsed with delipidated B16-F10 cells (FIG. 4). The slight reduction could be due to the DCs present in the localized area of vaccination taking up the delipidated B16-F10 cells and processing them (as demonstrated in FIGS. 1 and 2). Overall, this experiment demonstrated that vaccination with delipidated B16-F10 cells alone or as a dendritic cell hybrid protected against a pre-existing B16 melanoma with differing extents.

EXAMPLE 5

In Vitro Studies—Preventative Vaccination

To test whether DCs pulsed with delipidated B16-F10 cells had any benefit in preventing mice from developing B16 cancers, mice were vaccinated once as described below and challenged with B16-F10 cancer cells.

Briefly, cancer cells to be utilized, for example B16-F10 cells consisted of:

a) cells delipidated using the method of the instant invention, for example a solvent mixture of 3% DIPE and 0.05% TRITON X-100; or b) B16-F10 cells that were lysed using multiple freeze-thaw cycles.

Figure 12:
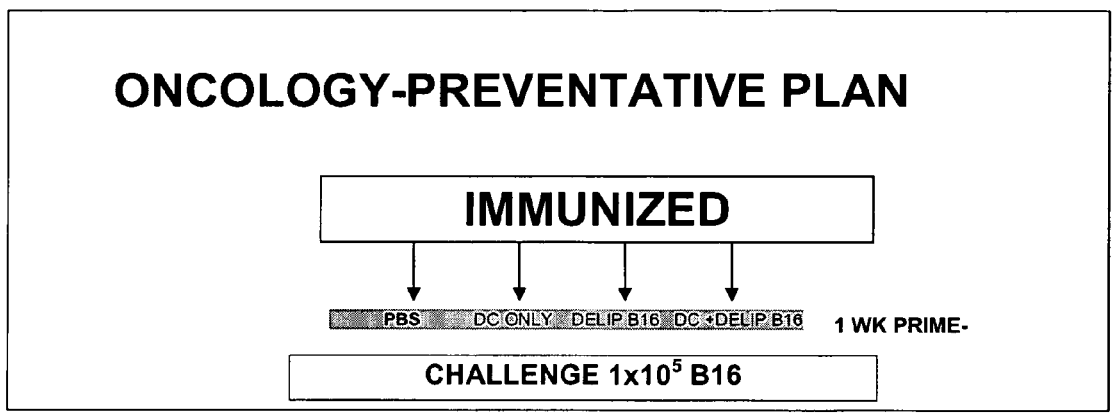
FIG. 12 is a schematic of the preventative vaccination experimental plan.

In Vivo mice inoculations were then performed using the following test groups (5 mice per group): A. mice unimmunized (PBS); B. mice immunized with $2\times10^5$ BMDDC only; C. mice immunized with $2\times10^5$ delipidated B16-F10 cells only; D. mice immunized with BMDDC pulsed with delipidated B16-F10 cells. The mice were challenged on day 6 after immunization by injecting $5\times10^5$ B16-F10 cells subcutaneously in the opposite flank. The experimental plan is shown in FIG. 12.

Figure 5:
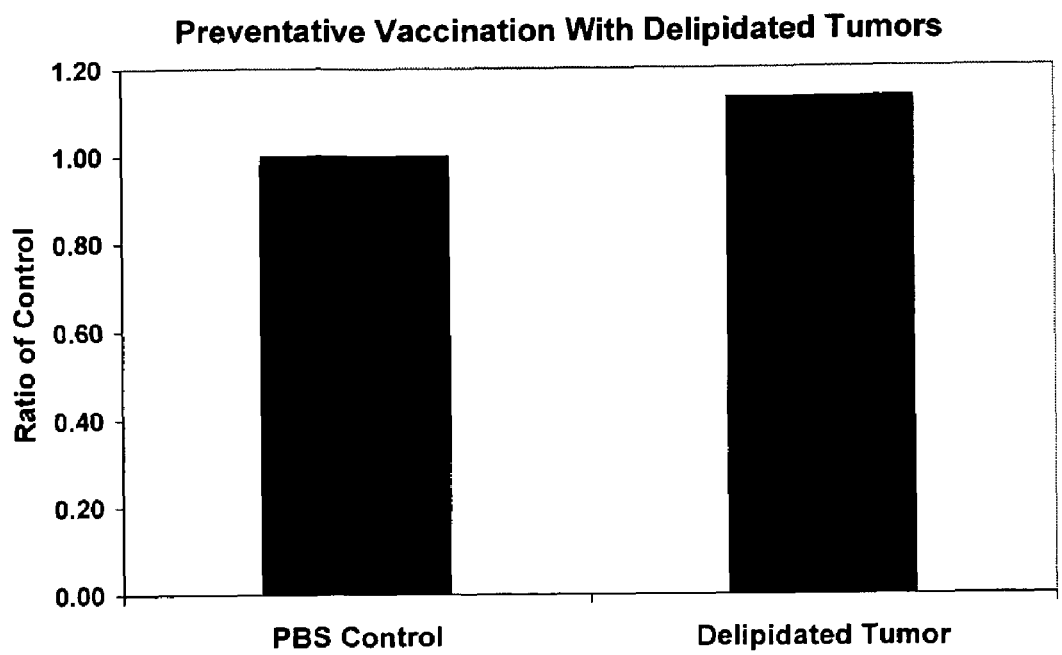
FIG. 5 depicts preventative vaccination using delipidated B16-F10 cancer cells.
Figure 6:
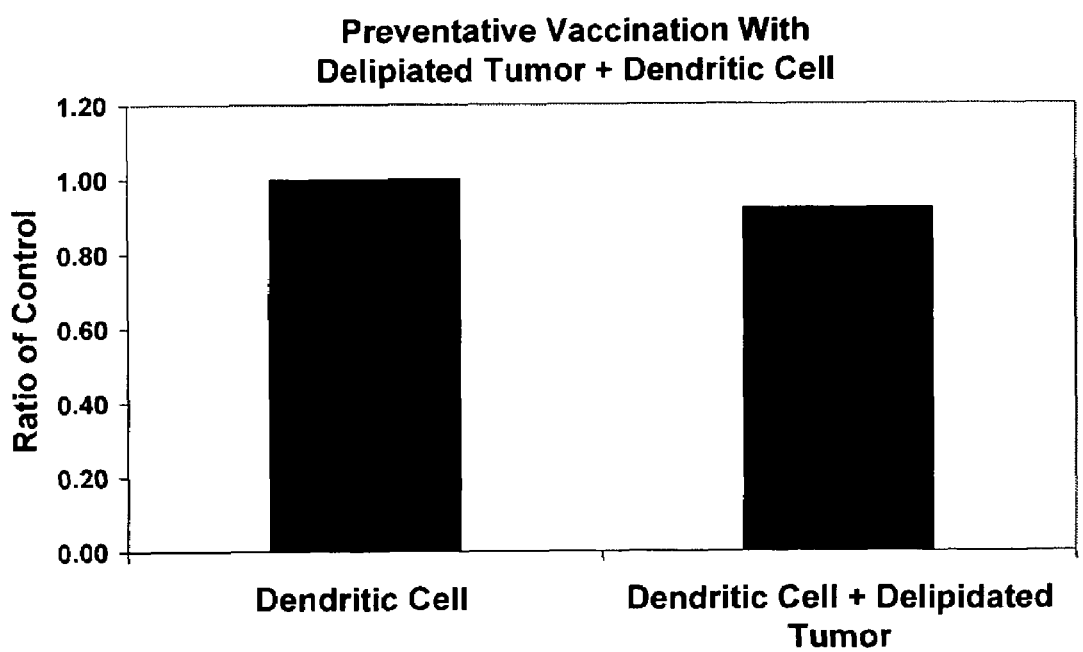
FIG. 6 is similar to FIG. 5 and depicts preventative vaccination using DCs and delipidated B16-F10 cancer cells.

The experiments indicated that vaccination with DCs pulsed with delipidated B16-F10 cells did not adequately protect mice from a challenge with B16-F10 cancer cells (FIGS. 5 and 6). However, we noted that B16-F10 melanomas are considered a poor immunogenic tumor model, because they do not efficiently trigger an immune response. Therefore, we speculate that multiple rounds of vaccination may be effective in a preventative cancer model.

EXAMPLE 6

Therapeutic Vaccination and Cancer Antigen Specific Immune Response

To determine whether vaccination with either delipidated B16-F10 cells or DCs pulsed with delipidated B16-F10 cells generated a tumor antigen specific immune response, antibody titers to B16 specific tumor antigens GP 100 and TRP-2 were measured.

An ELISA Assay was performed on Mouse Serum Samples as follows:

To coat the plates, peptides were diluted to 5 μg/ml in coating buffer (50 mM Tris, pH 9.5). Each well was coated with 100 μL/well on Nunc Immulon HBX 96 well ELISA plates. Each plate was sealed and incubated overnight. Protein was removed from the wells by flicking the plate and blotting on paper towels.

To block the plates, 200 μL blocking buffer (2% FBS, 1×PBS) was added to all wells. Each plate was sealed and incubated 1-2 hours at 37° C. Each well was washed six times with 150 μL wash buffer (1×PBS, 0.05% Tween-20).

Primary Antibody was prepared as followed. Briefly, a 1:20 dilution of mouse serum sample in sample dilution buffer (1×PBS, 5% Normal Goat Serum (NGS)) was prepared. Dilutions of 1:200, 1:400, 1:1000 and 1:2000 were prepared. The plates were coated with 50 μL diluted serum and incubated at room temperature for 60 minutes. The plates were washed six times with 150 μL wash buffer Secondary Antibody was prepared as followed. Briefly, the secondary antibody (Goat anti-mouse-HRP Fc Specific from Sigma) was diluted 1:10,000 in sample dilution buffer. Each well was coated with 100 μl/well and incubated at room temperature for 45 minutes. The wells were washed six times with 150 μL wash buffer ELISA development required adding 100 μL of TMB Substrate (Sigma) to each well and incubated at room temperature for 5 minutes. The reaction was stopped with 100 μL 1N $H_2SO_4$. The plates were read on a plate reader at absorbance 450 nm.

Figure 7:
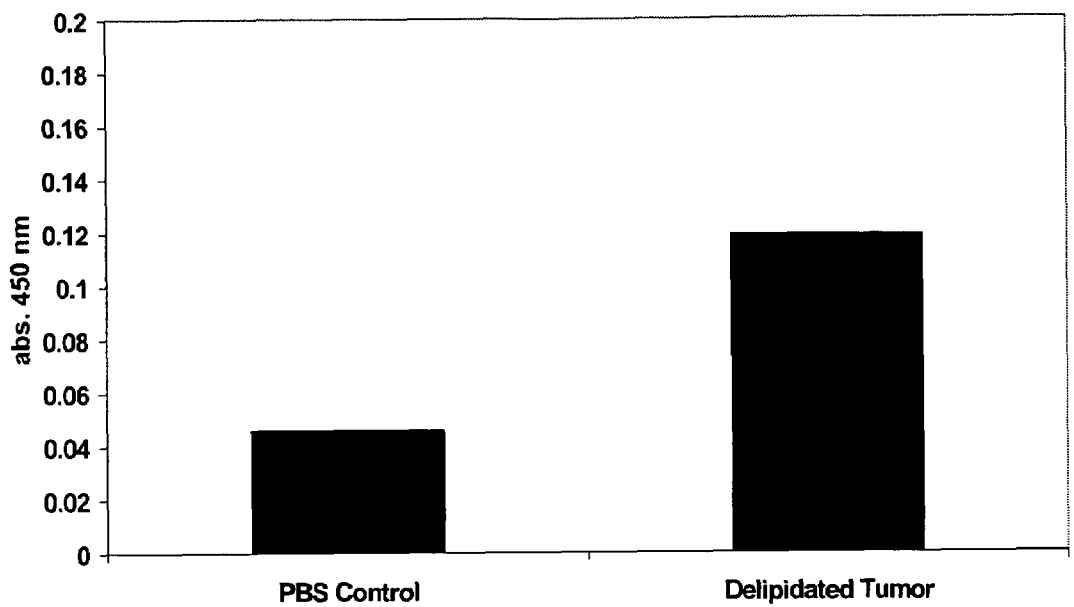
FIG. 7 depicts therapeutic vaccination using delipidated B16-F10 cancer cells to induce an antigen specific response.
Figure 8:
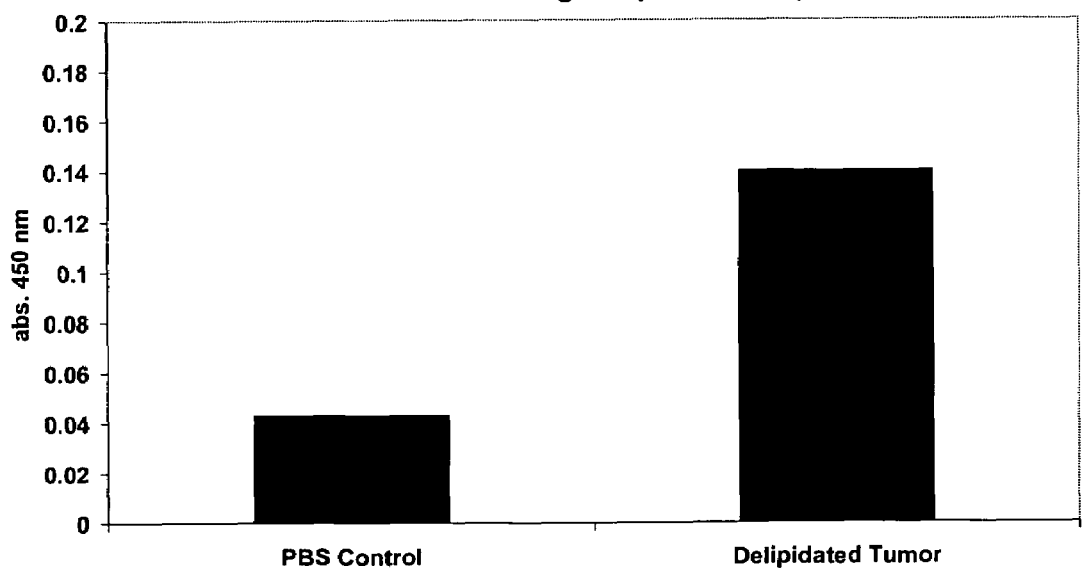
FIG. 8 depicts therapeutic vaccination using delipidated B16-F10 cancer cells to induce an antigen specific response.
Figure 9:
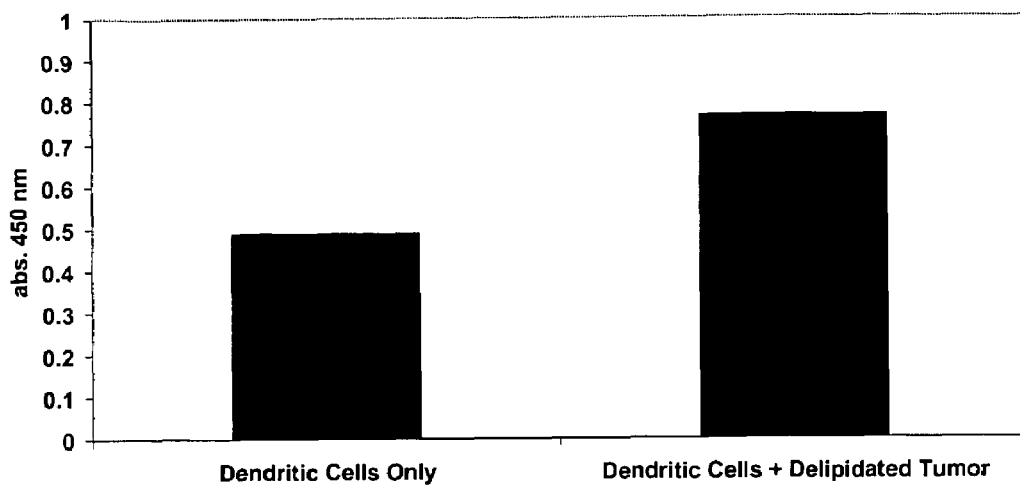
FIG. 9 depicts therapeutic vaccination using DCs and delipidated B16-F10 cancer cells to induce an antigen specific response.
Figure 10:
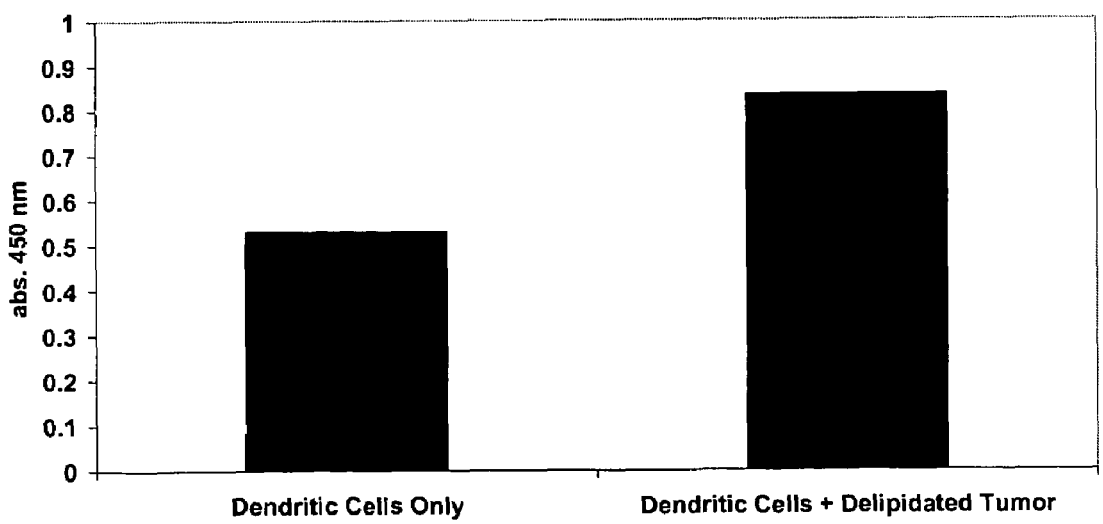
FIG. 10 depicts therapeutic vaccination using DCs and delipidated B16-F10 cancer cells to induce an antigen specific response.

Vaccination with delipidated B16-F10 cells was observed to generate higher antibody titers than the control group vaccinated with PBS (FIGS. 7 and 8). However, the DC pulsed with delipidated B16-F10 cells had a much higher overall antibody titer (FIGS. 9 and 10), indicating that the DC pulsed with delipidated B16-F10 cells substantially enhanced antigen processing and presentation. Antibody titers in animals receiving DCs pulsed with delipidated B16-F10 cells were much higher than titers in animals vaccinated with DCs alone. The results demonstrate that delipidated B16-F10 cells are efficiently processed and presented by DCs, which leads to an enhanced immune response. Vaccination with DC alone was also observed to enhance antibody responses (FIGS. 9 and 10), possibly due to the incoming DCs taking up already existing cancer cells and processing them for an immune response. However, the uptake, processing and/or presentation rates were lower than animals receiving DC pulsed with delipidated B16-F10 cells. Overall, we observed that delipidated B16-F10 cell vaccination enhanced antibodies to B16 tumor antigens TRP-2 and GP 100 (FIGS. 7 and 8). Furthermore, we noted that animals receiving DCs pulsed with delipidated B16-F10 cell vaccination displayed greatly enhanced antibody titers to B16 tumor antigens TRP-2 and GP 100 (FIGS. 9 and 10). Although we observed that mature DCs can take up already existing cancers from mice, process them and present them to the immune system, this process is not as efficient as when DCs are pulsed with the delipidated B16-F10 cells.

EXAMPLE 7

In Vivo Experimental Protocol for Harvest and Growth of Bone Marrow Derived Dendritic Cells The following describes a method for the in vivo harvesting and growth of bone marrow derived dendritic cells (BMDDC). In this experiment the mouse species used was C57BL/6, approximately 8-16 weeks old. Five mice were assigned to each group. The cancer model in this experiment was a B16-F10 melanoma (in C57BL/6 mice), known to be a poorly immunogenic tumor model. Bone marrow was harvested from femurs and tibiae through a Falcon 100-μm nylon cell strainer.

Bone Marrow Preparation: Femurs and tibiae of female, 4-12 week old C57BL/6 mice were removed and purified from the surrounding muscle tissue by rubbing with Kleenex tissues. Intact bones were left in 70% ethanol for 2-5 minutes for disinfection and washed with PBS. Both ends of the bones were cut with scissors and the marrow flushed with PBS using a Syringe with a 0.45 mm diameter needle. Vigorous pipetting was used to disintegrate clusters within the marrow suspension. The suspension was then washed once with PBS. The cells were resuspended in (R10) RPMI-1640 (GIBCO BRL) supplemented with Penicillin (100 U/mL, Sigma), Streptomycin (100 U/mL, Sigma), L-glutamine (2 mM, Sigma), 2-mercaptoethanol (50 uM, Sigma), 10% heat-inactivated and filtered Fetal Calf Serum all filtered through a (0.22 uM, Millipore or Corning Filter)

Day 0: Seed Bone Marrow. Leukocytes were seeded at $2 \times 10^6$ per 100 mm dish in 10 ml R10 medium containing 200 U/ml (=20 ng/ml) rmGM-CSF.

Day 3: Another 10 ml of R10 medium containing 200 U/ml rmGM-CSF was added.

Day 6: Half of the culture supernatant was collected, the removed culture supernatant was centrifuged, and the pellet was resuspended in 10 ml of fresh R10 medium containing 200 U/ml rmGM-CSF. The suspension was re-plated back onto the original plate.

Day 7: The immature DCS were fed with lysed or delipidated B16-F10 cells. Add $1 \times 10^6$ DC and $1 \times 10^6$ delipidated B16-F10 cells for 24 hours.

Complete Maturation:

Day 8: The DC and delipidated B16-F10 cells were matured using Lipid A at 100 ng/ml or lipopolysaccharide (LPS) at 1 ug/ml+30-100 U/ml rm (recombinant murine) GM-CSF. The cells were incubated for an additional 24 hrs prior to injection.

Cell yield evaluation: Cultured cells were washed once. An aliquot of cells was mixed 1:1 (vol:vol) with trypan blue Solution (Sigma). Trypan blue negative, large leukocytes (erythrocytes excluded by size and shape) were counted as viable under the microscope.

FACS Analysis $1 \times 10^5$ cells were stained with 50 μl hybridoma culture supernatants containing 0.1% sodium azide or purified first and second step antibodies see MB. Lutz et al. *Journal of Immunological Methods* 223 (1999) 77-92 79. The cells and primary and secondary antibody (5-20 μg/ml) were incubated for 30 min on ice. Both primary and secondary reagents were diluted in PBS containing 5% fetal calf serum (FCS) and 0.1% sodium azide, which also served as washing medium. Samples were analyzed with a FACScan (Becton Dickinson, Heidelberg, Germany).

The following antibodies were used for surface and cytoplasmic staining as culture supernatants reviewed in Leenen et al., 1997: MHC molecules: H-2 K-FITC_M1r42, rat IgG2a; (Pharmingen, San Diego, Calif.); co-stimulatory adhesion molecules: CD80_B7-1-PE, 16-10A1, hamster IgG, (Pharmingen), CD86_B7-2-FITC, GL1, rat IgG2a, (Pharmingen); CD40-PE-HM40-3, rat IgG2b, (Pharmingen). DC markers: CD25_IL-2Ra, 7D4, rat IgM, NLDC-145 DEC-205, rat IgG2a, CD11c PE_HL3, hamster IgG-PE, G235-2356 (Pharmingen).

Endocytotic capacity of BMDDC was investigated as described in detail elsewhere, see Sallusto et al., 1995 and Lutz et al., 1997. Briefly, $2 \times 10^5$ cells were incubated with FITC-DX at 1 mg/ml on ice surface binding but no endocytosis or in a 37° C. surface binding and endocytosis waterbath for 30 min. Cells were washed with ice cold PBS and stained for surface MHC class II molecules as described above.

Whole bone marrow cells were plated in six-well plates in complete IMDM (2 mM glutamax, 100 U/ml penicillin, 100 ug/ml streptomycin, 50 uM 2-ME, and 5% FCS) supplemented with 10 ng/ml murine GM-CSF, and 20 ng/ml murine IL-4. Cultures were fed every 2-3 days by removing 50% of medium from each well and adding back an equal amount of fresh growth factor supplemented cIMDM. The cultures were maintained for 6-8 days. Non adherent and loosely adherent cells were harvested, washed and used for in vitro and in vivo experiments.

All patents, publications and abstracts cited above are incorporated herein by reference in their entirety. It will be appreciated that other embodiments and uses will be apparent to those skilled in the art and that the invention is not limited to these specific illustrative examples or preferred embodiments. It should be understood, of course, that the foregoing relates only to preferred embodiments of the present invention and that numerous modifications or alterations may be made therein without departing from the spirit and the scope of the invention as set forth in the appended claims.

The invention claimed is:

1. A composition comprising: a modified cancer cell with reduced lipid content, as compared to an unmodified cancer cell of the same cancer type and at least one cancer cell antigen; and, a pharmaceutically acceptable carrier.

2. The composition of claim 1, further comprising a dendritic cell.

3. The composition of claim 1, further comprising an immunostimulant.

4. The composition of claim 2, further comprising an immunostimulant.

5. The composition of claim 1, wherein the modified cancer cell is immunogenic when administered to an animal or an human.

6. The composition of claim 2, wherein the modified cancer cell is immunogenic when administered to an animal or an human.

7. A composition comprising a modified cancer cell with reduced lipid content as compared to an unmodified cancer cell of the same cancer type and at least one cancer cell antigen.

8. A composition comprising a modified cancer cell with reduced lipid content, as compared to an unmodified cancer cell of the same cancer type, and at least one cancer cell antigen, wherein the reduced lipid content in the modified cancer cell is reduced by at least 20% as compared to the unmodified cancer cell.

9. The composition of claim 7, wherein the modified cancer cell is produced by exposing the unmodified cancer cell to a process comprising treating the unmodified cancer cell with 0.1% to 50% of a first extraction solvent.

10. The composition of claim 9, wherein the first extraction solvent is an ether, an alcohol, or a combination thereof.

11. The composition of claim 10, wherein the ether is diisopropylether and the alcohol is butanol.

12. A method for reducing levels of lipid in a cancer cell comprising:
   contacting a cancer cell in a fluid with a first extraction solvent;
   mixing the fluid and the first extraction solvent for a sufficient time to extract lipid from the cancer cell, thereby producing a cancer cell with reduced lipid content;
   extracting the solvent layer from the fluid; and,
   collecting the fluid containing the cancer cell with reduced lipid content.

13. The method of claim 12, wherein the amount of lipid present in the cancer cell with reduced lipid content is reduced by at least 20% as compared to a non-delipidated cancer cell.

14. The method of claim 12, wherein the wherein the first extraction solvent is an ether, an alcohol, or a combination thereof.

15. The method of claim 14, wherein the ether is diisopropylether and the alcohol is butanol.

16. A method for delipidation of cancer cells comprising:
   exposing a cancer cell to a delipidation process, comprising treating the cancer cell with one or more extraction solvents such that the amount of lipid present in the cancer cell is reduced by at least 20% as compared to a non-delipidated cancer cell, wherein the cancer cell with reduced lipid content retains at least one cancer cell antigen.

17. A method for promoting antibody production to the at least one cancer cell antigen in an animal or human comprising administering to the animal or the human the composition of claim 1.

18. A method for promoting antibody production to the at least one cancer cell antigen in an animal or human comprising administering to the animal or the human the composition of claim 2.

* * * * *